(12) United States Patent
Korenberg

(10) Patent No.: US 9,131,864 B2
(45) Date of Patent: Sep. 15, 2015

(54) SYSTEM AND METHOD FOR EVALUATING AN ELECTROPHYSIOLOGICAL SIGNAL

(71) Applicant: 8825319 Canada Limited, Battersea (CA)

(72) Inventor: Michael Korenberg, Battersea (CA)

(*) Notice: Subject to any disclaimer, the term of this patent is extended or adjusted under 35 U.S.C. 154(b) by 0 days.

(21) Appl. No.: 13/959,030

(22) Filed: Aug. 5, 2013

(65) Prior Publication Data

US 2014/0194758 A1 Jul. 10, 2014

Related U.S. Application Data

(63) Continuation-in-part of application No. PCT/US2012/024037, filed on Feb. 6, 2012.

(60) Provisional application No. 61/462,640, filed on Feb. 4, 2011.

(51) Int. Cl.
*A61B 5/04* (2006.01)
*A61B 5/044* (2006.01)
*A61B 5/00* (2006.01)
*A61B 5/0452* (2006.01)
*A61B 5/0245* (2006.01)
(Continued)

(52) U.S. Cl.
CPC ......... *A61B 5/04012* (2013.01); *A61B 5/02028* (2013.01); *A61B 5/0245* (2013.01); *A61B 5/044* (2013.01); *A61B 5/046* (2013.01); *A61B 5/04011* (2013.01); *A61B 5/0452* (2013.01); *A61B 5/0464* (2013.01); *A61B 5/04525* (2013.01); *A61B 5/055* (2013.01); *A61B 5/4848* (2013.01); *A61B 5/7203* (2013.01); *A61B 5/7253* (2013.01); *A61B 6/032* (2013.01); *G06K 9/0051* (2013.01); *G06K 9/00536* (2013.01); *A61B 5/4884* (2013.01); *A61B 5/7232* (2013.01); *A61B 5/7239* (2013.01)

(58) Field of Classification Search
CPC ...... A61B 5/04; A61B 5/0205; A61B 5/7257; A61B 5/7253; A61B 5/04023
USPC ....................................................... 600/509
See application file for complete search history.

(56) References Cited

U.S. PATENT DOCUMENTS 4,723,536 A 2/1988 Rauscher et al.
6,325,761 B1* 12/2001 Jay .................................. 600/485
(Continued)

OTHER PUBLICATIONS

The College Mathematics Journal, vol. 31, No. 2, (2000), pp. 82-887, Marcia Kleinz and Thomas J. Osler.*
(Continued)

*Primary Examiner* — Robert N Wieland

(57) ABSTRACT

A method of evaluating an electrophysical signal. The method utilizes a model-derived reconstruction over at least one cycle of the electrophysical signal to identify a pathological event, whereby at least one term in the model is differentiable. The invention is also directed to a non-transitory computer readable medium having instructions stored thereon for identifying a pathological event from a model-derived reconstruction of an electrophysical signal. The invention is further directed to a system for evaluating an electrophysical signal. The system includes a processor configured to identify a pathological event from a model-derived reconstruction of the electrophysical signal, a data input coupled to the processor for providing the processor with the electrophysical signal, and a user interface.

20 Claims, 21 Drawing Sheets

(51) Int. Cl.
*A61B 5/046* (2006.01)
*A61B 5/0464* (2006.01)
*A61B 5/02* (2006.01)
*A61B 5/055* (2006.01)
*A61B 6/03* (2006.01)
*G06K 9/00* (2006.01)

(56) References Cited

U.S. PATENT DOCUMENTS

| | | |
|---|---|---|
| 2004/0059203 A1 | 3/2004 | Guerrero et al. |
| 2004/0230105 A1 | 11/2004 | Geva et al. |
| 2008/0027341 A1 | 1/2008 | Sackner et al. |
| 2009/0292180 A1 | 11/2009 | Mirow |
| 2013/0096394 A1 | 4/2013 | Gupta |

OTHER PUBLICATIONS

Efron, Bradley, et al., "Least Angle Regression", The Annals of Statistics, 2004, vol. 32, No. 2, pp. 407-499.

Tibshirani, Robert, "Regression Shrinkage and Selection via the Lasso", Journal of the Royal Statistical Society. Series B (Methodological), 1996, vol. 58, Issue 1, pp. 267-288.

Korenberg, Michael J., "Identifying nonlinear difference equation and functional expansion representations: the fast orthogonal algorithm", Annals of Biomedical Engineering, 1988, vol. 16, No. 1, pp. 123-142.

Korenberg, Michael J., "Fast orthogonal identification of nonlinear difference equation and functional expansion models", Proceedings of the 1987 30th Midwest Symp Circuit Sys (in Syracuse, New York), 1988, vol. 1, pp. 270-276.

Korenberg, Michael J., "A Robust Orthogonal Algorithm for System Identification and Time-Series Analysis", Biological Cybernetics, 1989, vol. 60, pp. 267-276.

Korenberg, Michael J., "Fast orthogonal algorithms for nonlinear system identification and time-series analysis", in Advanced Methods of Physiological System Modeling, vol. II, edited by V. Z. Marmarelis. Los Angeles: Biomedical Simulations Resource, 1989, pp. 165-177.

Korenberg, Michael J., et al., "Applications of Fast Orthogonal Search: Time-Series Analysis and Resolution of Signals in Noise", Annals of Biomedical Engineering, 1989, vol. 17, pp. 219-231.

Adeney, Kathryn M., et al.,"Fast orthogonal search for array processing and spectrum estimation", 1994, IEE Proc.-Vis. Image Signal Process. vol. 141, No. 1, pp. 13-18.

Korenberg, Michael J., et al. "Iterative Fast Orthogonal Search for Modeling by a Sum of Exponentials or Sinusoids", Annals of Biomedical Engineering, 1998, vol. 26, pp. 315-327.

Chon, Ki H., "Accurate Identification of Periodic Oscillations Buried in White or Colored Noise Using Fast Orthogonal Search", 2001, IEEE Transactions on Biomedical Engineering, vol. 48, No. 6, pp. 622-629.

Gupta, S., et al., "Complex Sub-Harmonic Structures As a Predictor for ICD Therapy", 2010, Canadian Cardiovascular Congress (CCC), No. 208, Montreal, Quebec, Canada, Oct. 23-27.

Atia, Mohamed M., et al., "Fast features reduction of radio maps for real-time fingerprint-based wireless positioning systems", Electronics Letters, 2011, vol. 47, No. 20, pp. 1151-1153.

Perry, Alexander. G., et al., "Modeling and Syndromic Surveillance for Estimating Weather-Induced Heat-Related Illness", Journal of Environmental and Public Health, 2011, vol. 2011, Article ID 750236, 10 pages, doi:10.1155/2011/750236).

Kleinz, Marcia, et al., "A Child's Garden of Fractional Derivatives", The College Mathematics Journal, Mar. 2000, vol. 31, No. 2, pp. 82-88.

Korenberg, Michael J., "Parallel Cascade Identification and Kernel Estimation Estimation for Nonlinear Systems", Annals of Biomedical Engineering, 1991, vol. 19, pp. 429-455.

Abbas, Hazem M., "Time series analysis for ECG data Compression," Proc. of the IEEE Intl. Conf. On Acoustics, Speech, and Signal Processing-ICASSP-99, Mar. 1999, Phoenix-AZ, pp. 1537-1540.

International Search Report, dated Jun. 15, 2012, received in connection with corresponding International Patent Application No. PCT/US2012/024037.

\* cited by examiner

SYSTEM AND METHOD FOR EVALUATING AN ELECTROPHYSIOLOGICAL SIGNAL

RELATED APPLICATIONS

This application claims priority to PCT Application No. PCT/US2012/24037, filed Feb. 6, 2012, entitled "System and Method for Evaluating an Electrophysiological Signal," which claims priority to U.S. Provisional Application Ser. No. 61/462,640, filed Feb. 4, 2011, entitled "Phase Space and Enhanced Fast Orthogonal Search Used For Electrocardiogram Pathology Detection." The disclosures of the above-identified applications are hereby incorporated by reference in their entirety.

BACKGROUND OF THE INVENTION

1. Field of the Invention

The claimed invention relates to methods and systems for evaluating an electrophysiological signal.

2. Description of Related Art

Frequently, important physiological information can be captured as electrophysiological signals. Some examples include, but are not limited to, electrocardiogram (ECG) signals, voiced speech signals, electrooculogram (EOG) and electromyogram (EMG) signals, vestibuloocular response signals, blood pressure gamma synchrony signals (based on electroencephalogram (EEG) measurements), a respiratory function signal, a pulse oximetry signal (measuring the oxygenation of a patient's blood), a perfusion data signal (measuring changes in tissue images following introduction of a contrast agent to the blood), and quasi-periodic biological signals.

The article by Korenberg and Paarmann ("Applications of Fast Orthogonal Search: Time-Series Analysis and Resolution of Signals in Noise", Ann. Biomed. Eng., Vol. 17, pp. 219-231, 1989), which is hereby incorporated by reference in its entirety, specifically relates the application of Fast Orthogonal Search (FOS) to several of the above electrophysiological signals, including ECG, EEG, EOG, and EMG signals, and shows that FOS can recover signals heavily contaminated with noise. In particular FOS is applied to the signal, a plurality of nonlinear terms (e.g. sinusoidal functions) are generated corresponding to the signal, a noise component is separated from the plurality of nonlinear terms corresponding to the signal, and a reconstructed signal is formed whereby the noise component is removed by using a subset of the plurality of nonlinear terms corresponding to the signal (see Example 3: Noisy Data Case, and FIGS. 1-3, on pages 228-230 of this article). The article discloses that FOS can be used to find accurate and parsimonious sinusoidal series models for such electrophysiological signals. FOS finds the terms in the series by searching through a set of candidate terms. The sinusoidal series developed in the article, sums of cosine and sine functions, are examples of summation series of complex exponentials. Here a cosine can be the real part, and a sine can be the imaginary part, of a complex exponential. It should be noted that the sinusoidal terms in such series are fractionally differentiable and integrable analytically, where the order of the fractional derivative or integral can be any real or complex number. A derivative of negative order $-a$, where $a > 0$, corresponds to an integral of positive order $a$. A derivative of zero order of a function is just the function itself.

In the article by Adeney and Korenberg (IEE Proc.-Vis. Image Signal Process. Vol. 141, No. 1, pp. 13-18, 1994), which is hereby incorporated by reference in its entirety, FOS and Iterative FOS (IFOS) are used to find a sum of complex sinusoids, which is also a summation series of complex exponentials. Both FOS and IFOS are shown to be very powerful methods for dealing with noise contamination, for signal-to-noise ratios (SNR) as low as −10 dB.

Chon (IEEE TRANSACTIONS ON BIOMEDICAL ENGINEERING, VOL. 48, NO. 6, pp 622-629, June 2001) also shows that FOS can be used to detect periodic frequency components in both cardiovascular and renal signals, separating these components "from the unwanted stochastic component (noise source)". FOS was shown to be effective even when the SNR was as low as −20 dB, and was "undeterred by the adverse effects of colored, white and 1/f noise present in the data".

U.S. Pat. No. 6,325,761 (Dec. 4, 2001) to Jay discloses a device and method for measuring pulsus paradoxus ("a quantifiable, exaggerated decrease in arterial blood pressure during inspiration"), using as input data a waveform indicative of patient pulsatile cardiovascular behavior from an optical plethysmograph, a pulse oximeter, or a blood pressure monitor. The invention can assess the status of a patient in acute respiratory distress to determine severity of the condition, and one embodiment uses FOS to fit a sinusoidal series to the data for measurement of pulsus paradoxus and display. Thus the invention describes a method of evaluating an electrophysiological signal, including receiving an electrophysiological signal, obtaining a model-derived reconstruction using a summation series of complex exponentials (here a sinusoidal series) over at least one cycle of the electrophysiological signal to identify a pathological condition (pulsus paradoxus), and display on a user interface data indicative of pulsus paradoxus, and predict the risk for adverse clinical outcomes, such as impending severe respiratory distress.

Before U.S. Provisional Application Ser. No. 61/462,640 was filed Feb. 4, 2011, a Gupta et al presentation (COMPLEX SUB-HARMONIC STRUCTURES AS A PREDICTOR FOR ICD THERAPY, Abstract at the Canadian Cardiovascular Congress, Montreal, Canada, Oct. 23-27, 2010) considered the use of FOS on high-resolution ECG data, and "Risk stratification for sudden cardiac death (SCD)". They hypothesized that "a contemporary algorithm" [they used FOS] "which is capable of detecting aperiodic complex sub-harmonic frequencies (CSF) may detect differences in the ECG spectra of patients demonstrating SCD potential when compared with controls" and provided supporting experimental results.

The human heart 20, schematically illustrated in FIG. 1, has four contractile chambers which work together to pump blood throughout the body. The upper chambers are called atria, and the lower chambers are called ventricles. The right atrium 22 receives blood 24 that has finished a tour around the body and is depleted of oxygen. This blood 24 returns through the superior vena cava 26 and inferior vena cava 28. The right atrium 22 pumps this blood through the tricuspid valve 30 into the right ventricle 32, which pumps the oxygen-depleted blood 24 through the pulmonary valve 34 into the right and left lungs 36, 38. The lungs oxygenate the blood, and eliminate the carbon dioxide that has accumulated in the blood due to the body's many metabolic functions. The oxygenated blood 40 returns from the right and left lungs, 36, 38 and enters the heart's left atrium 42, which pumps the oxygenated blood 40 through the bicuspid valve 44 into the left ventricle 46. The left ventricle 46 then pumps the blood 40 through the aortic valve 48 into the aorta 50 and back into the blood vessels of the body. The left ventricle 46 has to exert enough pressure to keep the blood moving throughout all the blood vessels of the body. The contractions of the heart's chambers are controlled by electrochemical mechanisms which generate an electrophysiological signal that can be measured. In the case of the heart, the electrophysiological signal can be captured as an electrocardiogram (ECG).

The human brain 52 is an even more complex part of the body, composed of bundles of electrically active neurons, and organized into functional regions such as the cerebrum 54, the brain stem 56, and the cerebellum 58 as schematically illustrated in FIG. 2. The cerebrum 54 is responsible for conscious behavior and has areas for motor, sensory, and association functions. The brain stem 56, which contains the medulla oblongata plays an important role as an autonomic reflex center involved in maintaining the body's homeostasis. In particular, this portion of the brain regulates heart rate, respiratory rhythm, and blood pressure. The cerebellum 58 processes neural impulses received from the cerebral motor cortex, various brain stem nuclei, and sensory receptors in order to appropriately control skeletal muscle contractions to enable smooth, coordinated movements. The neural activity of the brain also involves electrochemical mechanisms which generate an electrophysiological signal that can be measured. In the case of the brain, the electrophysiological signal can be captured as a electroencephalogram (EEG).

With the ongoing proliferation of data acquisition devices, more and more physiological aspects are able to be captured as electrophysiological signals. Some examples include, but are not limited to, gamma synchrony signals (based on EEG measurements), a respiratory function signal, a pulse oximetry signal (measuring the oxygenation of a patient's blood), a perfusion data signal (measuring changes in tissue images following introduction of a contrast agent to the blood), and quasi-periodic biological signals.

Devices which capture electrophysiological signals may be valuable tools for physicians to study the health conditions of a patient. After the recording of the electrophysiological signal, it is up to the physician or healthcare provider to perform the signal analysis. For example, in the case of ECG signal analysis, there are certain integrated automatic analysis processes and systems which automatically determine different types of heart beats, rhythms, etc. The traditional output from the existing ECG software is basic data that often needs to be supplemented by a Cardiac MRI (Magnetic Resonance Imaging), CT (Computed tomography) or a more invasive test. However, there are a number of limitations associated with all such systems described above, they are complex, their outputs are difficult to analyze, and such techniques are expensive to use.

In addition to the above systems, there are various time domain and frequency domain signal processing techniques which are being used for the analysis of electrophysiological signals to obtain more detailed information. Unfortunately, the time domain techniques are incapable of quantifying certain fluctuation characteristics of a number of pathologies related to the electrophysiological signal. For example, with regard to the heart, traditional methods for performing frequency-domain analysis of surface ECG signals, such as the Fourier transform, are limited since they do not address the random nature of biological and electromagnetic noise or the variation between patients.

For example, in case of arrhythmia, the heart generates very complex ECG waveforms that have a large variation in morphologies. Dominant frequency analysis on these ECGs can be problematic since non-linear dynamic systems can appear to generate random noise. Discrete fast Fourier transforms and wavelet analysis have been shown experimentally to be incapable of detecting deterministic chaos in the presence of strong periodicity which tends to obscure the underlying non-linear structures. Thus, the detection of complex sub-harmonic frequencies which are thought to exist in all arrhythmia requires dynamic non-linear analyses. Complex subharmonic frequencies are similarly thought to exist in other types of electrophysiological signals and may be indicative of other pathological events which are not otherwise detectable from the electrophysiological signal using prior art methods.

Therefore, there is a need for a reliable and efficient system and method for evaluating an electrophysiological signal to predict pathological events with high accuracy.

SUMMARY

A method of evaluating an electrophysiological signal is disclosed. A model-derived reconstruction over at least one cycle of the electrophysiological signal is used to identify a pathological event.

A non-transitory computer readable medium is also disclosed. The non-transitory computer readable medium has stored thereon instructions for identifying a pathological event from a model-derived reconstruction of an electrophysiological signal, which, when executed by a processor, causes the processor to perform steps comprising using a model-derived reconstruction over at least one cycle of the electrophysiological signal to identify a pathological event.

A system for evaluating an electrophysiological signal is also disclosed. The system includes a processor configured to identify a pathological event from a model-derived reconstruction of the electrophysiological signal. The system also includes a data input coupled to the processor and configured to provide the processor with the electrophysiological signal. The system further includes a user interface coupled to either the processor or the data input.

A method of evaluating an electrocardiogram (ECG) signal is further disclosed. A model-derived reconstruction of the ECG signal over at least one cycle of the ECG signal is used to identify a pathological event, wherein the model-derived reconstruction of the ECG signal comprises an an input/output (I/O) expansion of the ECG signal in which at least one of the terms of the I/O expansion is analytically differentiable.

A further method of evaluating an ECG signal is also disclosed. A model-derived reconstruction of the ECG signal over at least one cycle of the ECG signal is used to identify a pathological event, wherein the model-derived reconstruction of the ECG signal comprises a plurality of terms from a fast orthogonal search (FOS) or modified fast orthogonal search (MFOS) transformation of the ECG signal.

A further method of evaluating an electrophysiological signal is also disclosed. The electrophysiological signal is transformed to detect a plurality of non-linear terms corresponding to the electrophysiological signal. The electrophysiological signal is reconstructed using the plurality of non-linear terms, wherein the reconstructed electrophysiological signal has an incongruent part separated from the electrophysiological signal. A pathological event linked to the electrophysiological signal is determined by computing Lyapunov spectra with a continuous fast orthogonal search based Gram Schmidt orthogonalization.

Another method of evaluating an electophysio logical signal is disclosed. A fast orthogonal search (FOS) or modified fast orthogonal search (MFOS) transform is applied to the electrophysiological signal to generate a plurality of terms corresponding to the electrophysiological signal. A reconstructed electrophysiological signal is formed whereby a noise component is separated from the electrophysiological signal using a subset of the plurality of terms, corresponding to the electrophysiological signal, which have at least a desired compression ratio.

It is at least one goal of the claimed invention to provide an improved method which evaluates an electrophysiological signal to identify a pathological event. Other goals and advantages are noted herein.

Figure 1:
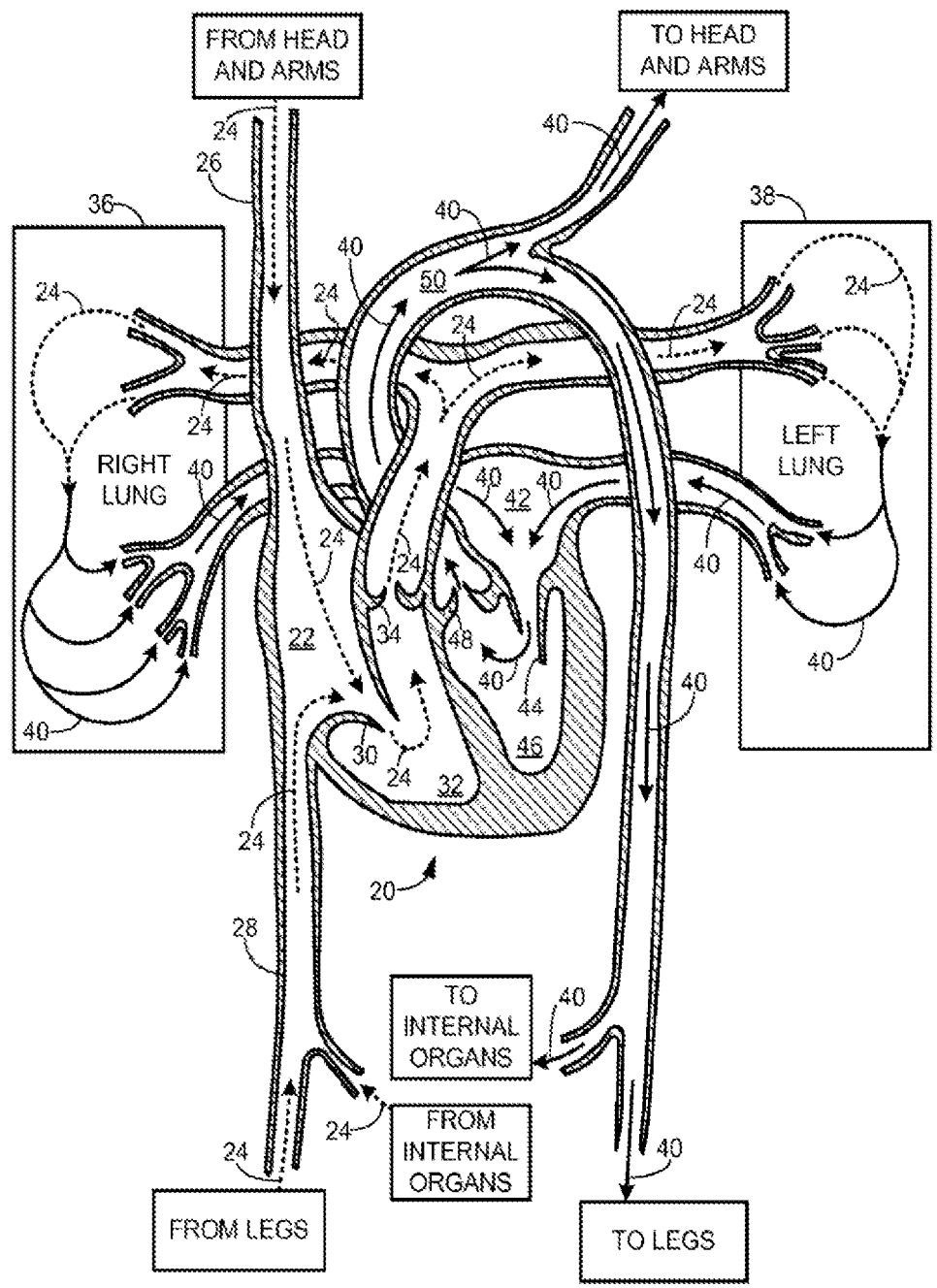
FIG. 1 schematically illustrates the operation of a human heart.
Figure 2:
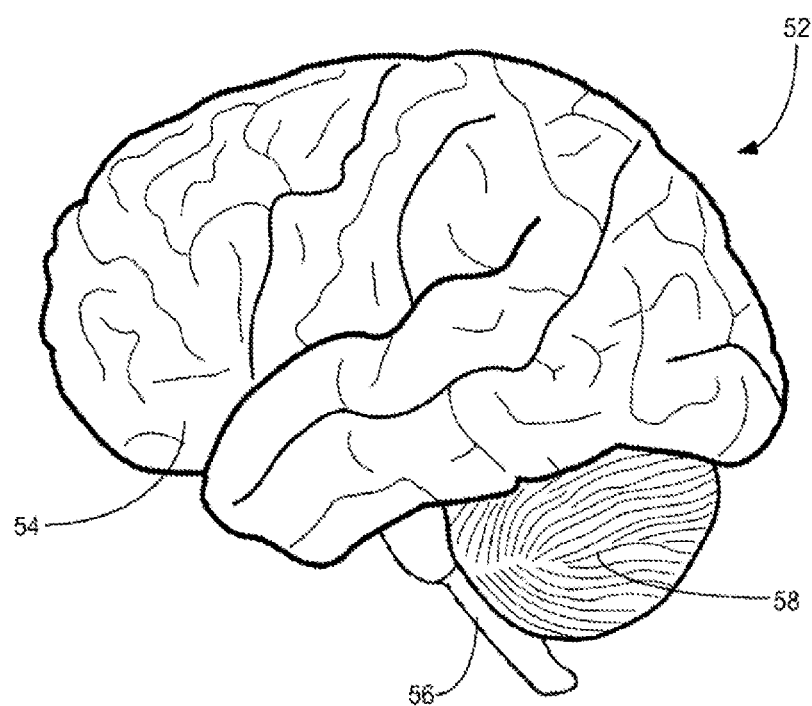
FIG. 2 schematically illustrates a human brain.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

As mentioned previously, there are numerous electrophysiological signals which may be captured from the body. Examples of electrophysiological signals include, but are not limited to an electrocardiogram (ECG), an electroencephalogram (EEG), a gamma synchrony signal, a respiratory function signal, a pulse oximetry signal, a perfusion data signal, a quasi-periodic biological signal, a fetal ECG, a blood pressure signal, and a heart rate signal. There is a proliferation of equipment for obtaining electrophysiological signals, but the ability of the prior art to identify pathological events from such signals has been limited as discussed above.

Embodiments of a method and system for evaluating an electrophysiological signal are disclosed herein. For convenience, the embodiments associated with FIGS. 3-11 will be discussed herein with respect to the evaluation of ECG electrophysiological signals, however, it should be understood by those skilled in the art that similar or equivalent embodiments may be applied to other types of electrophysiological signals.

Figure 3:
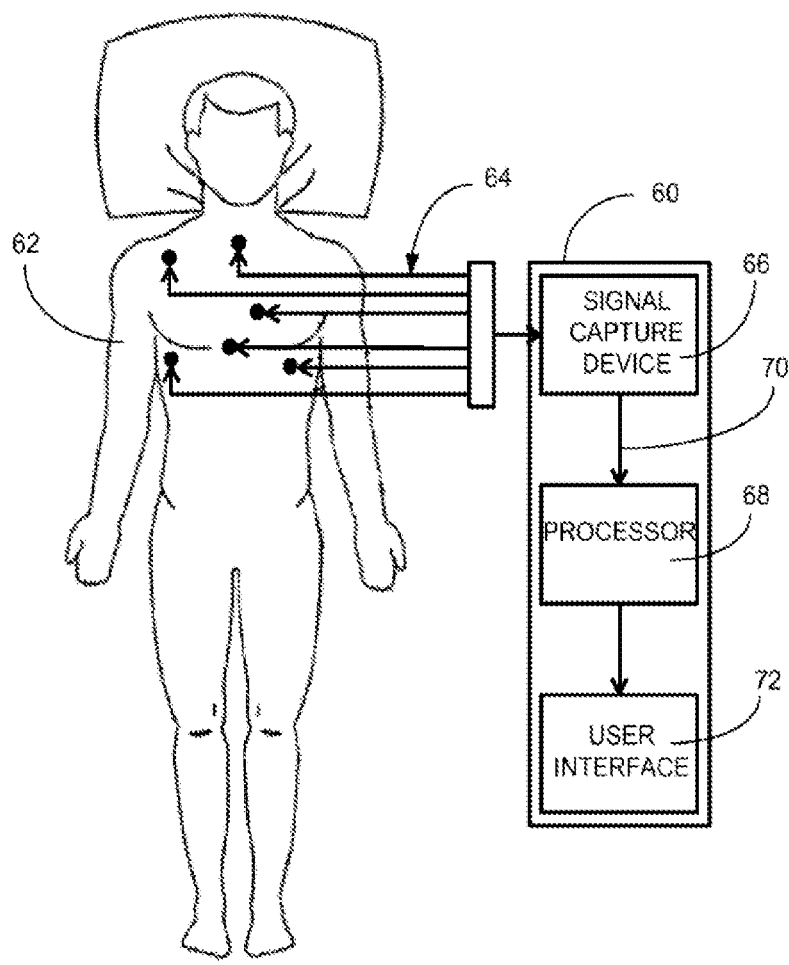
FIG. 3 is a block diagram depicting one embodiment of a system for evaluating an electrophysiological signal. In this embodiment, the electrophysiological signal comprises an ECG signal captured from a patient.

FIG. 3 schematically illustrates one embodiment of a system 60 which is used for the evaluation of ECG signal captured from a patient 62. In this embodiment, a plurality of electrodes 64 is placed over the patient's body to capture the ECG signal in three orthogonal channels mode. The ECG signals obtained from the plurality of electrodes 64 is collected by an electrophysiological signal capture device, for example a receiving module 66. In some embodiments, a Holier ECG monitor is used as the receiving module 66 for the recording of ECG signals. It should be appreciated that a person skilled in the art can also use any other method/device for the recording/capture of ECG signals. The recorded data from the ECG signal is made available to a processor 68 via a data input 70. The processor 68 may include a computer, a laptop, a distributed computer system or network, an application specific integrated circuit (ASIC), a programmable logic array (PLA), a microprocessor, digital circuitry, analog circuitry, or any combination and/or plurality thereof which has been specifically configured or programmed to perform the described embodied evaluation actions described herein and their equivalents. It should be noted that the data processing techniques described herein are not possible by mental processes and that one or more of the disclosed steps requires transformation of data by the processor 68 such that it is more than just a mental step. In this embodiment, the processor 68 uses a fast orthogonal search (FOS) process or a modified fast orthogonal search (MFOS) process for the processing of ECG data. The output of the processor 68 is then sent to a user interface/output module 72. The user interface 72 can be a display unit displaying the 3D phase space plot representation of the ECG data collected from the patient 62. As will be described further, the 3D phase plot can be used in some embodiments to help in locating the presence of complex sub-harmonic frequencies related to the abnormal conduction in the heart.

Figure 4A:
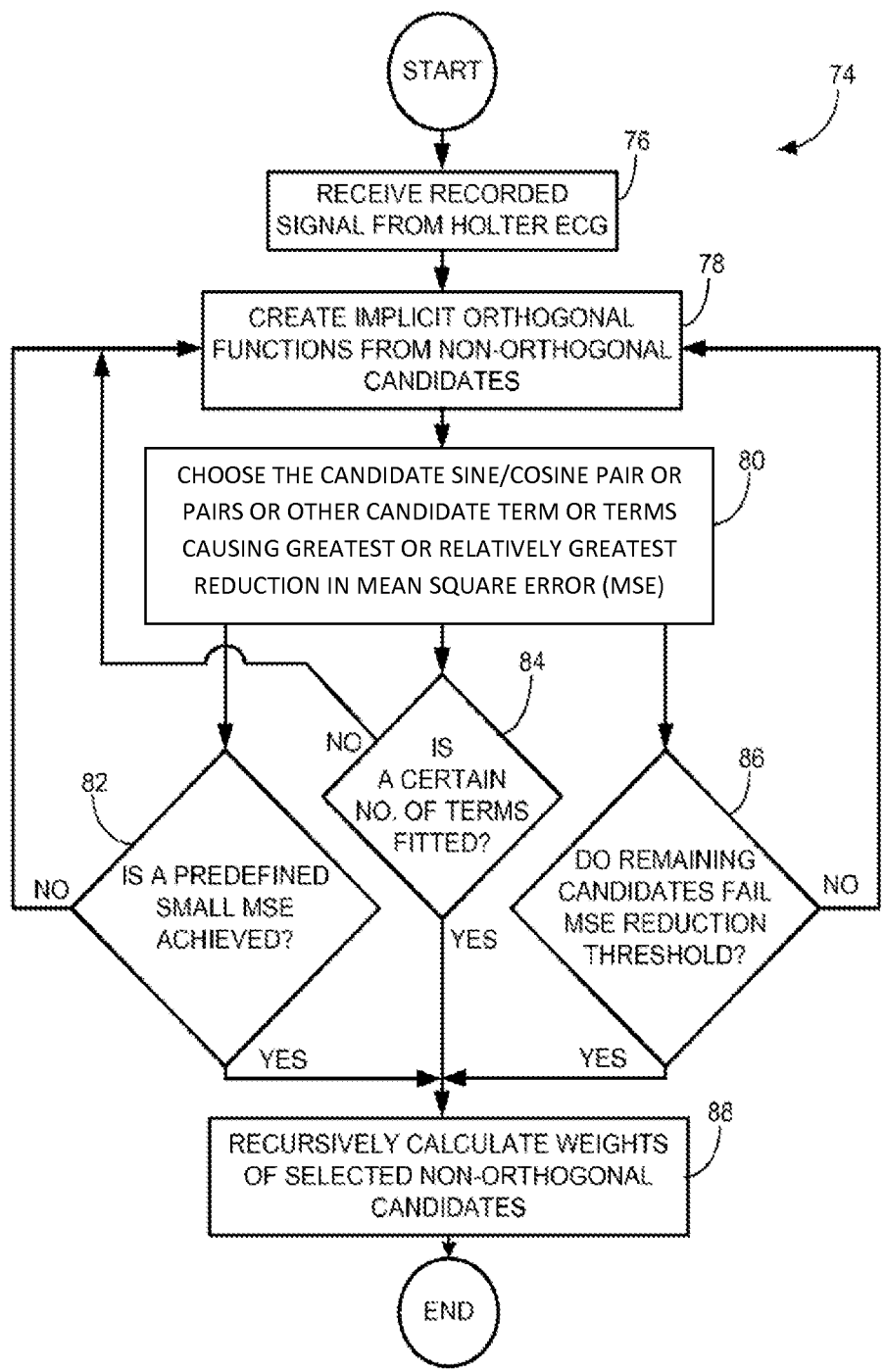
FIG. 4A-4C illustrate one embodiment of a modified fast orthogonal search (MFOS) transformation in accordance with an embodiment of the claimed invention.
Figure 4B:
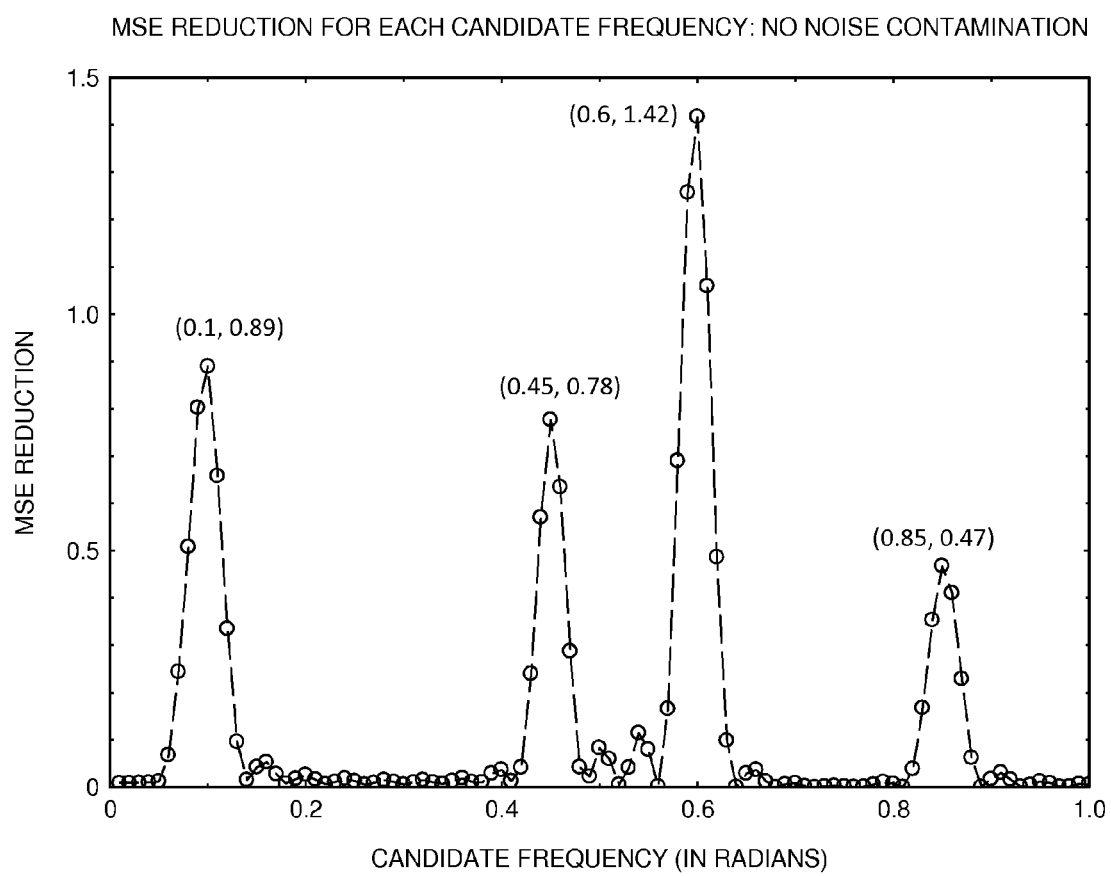
Figure 4C:
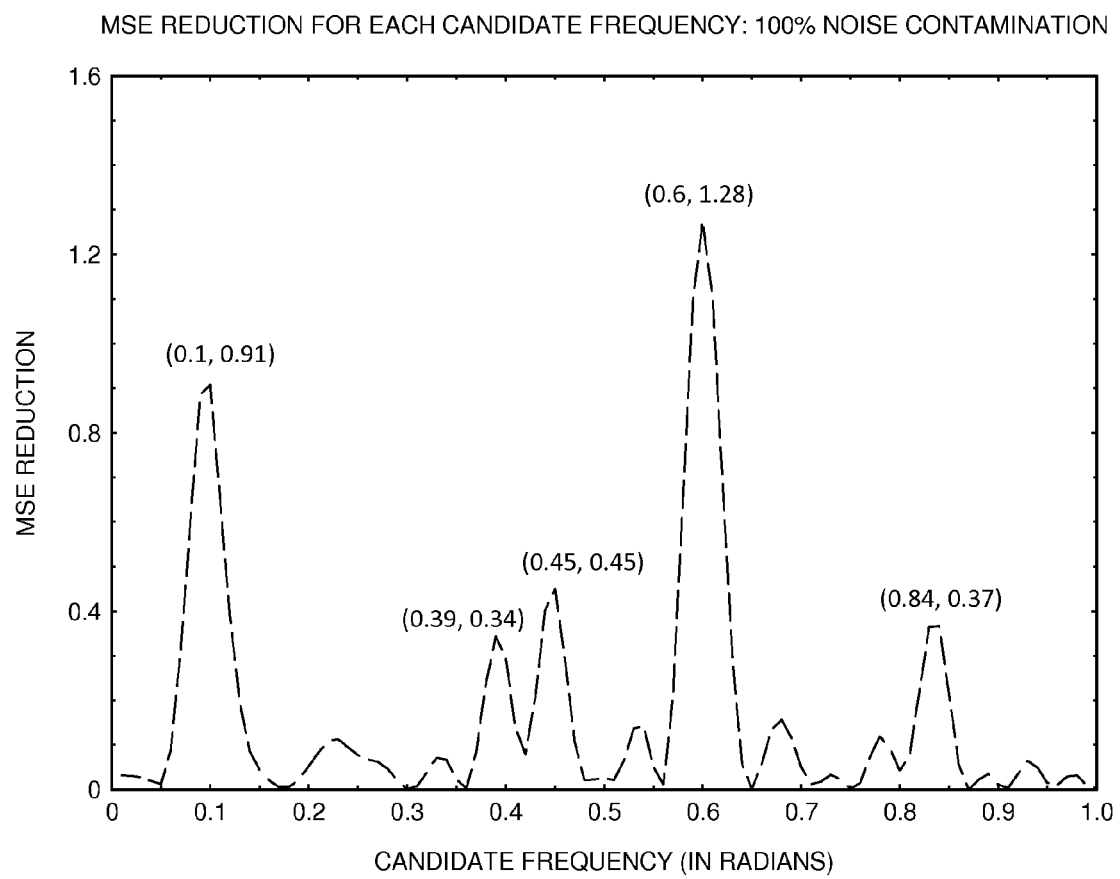

FIG. 4A-4C illustrate one embodiment of a modified fast orthogonal search (MFOS) process which can be used to produce a model-derived reconstruction. FIG. 4A is a flow chart 74 depicting the steps of one embodiment of the MFOS process which may be used to produce a model-derived reconstruction of the ECG signal according to some of the embodiments disclosed herein. The FOS process was introduced by the scientist M. J. Korenberg in "Identifying nonlinear difference equation and functional expansion representations: the fast orthogonal algorithm" in Annals of biomedical engineering 16(1): 123-42, 1988, in Korenberg M J, "Fast orthogonal identification of nonlinear difference equation and functional expansion models", Proc of the 1987 Midwest Symp Circuit Sys 1:270-276, in Korenberg, M. J. "A Robust Orthogonal Algorithm for System Identification and Time-Series Analysis" in Biological Cybernetics 60:267-276, 1989, and in the book chapter by Korenberg, M. J. "Fast orthogonal algorithms for nonlinear system identification and time-series analysis", in Advanced Methods of Physiological System Modeling, vol. II, edited by V. Z. Marmarelis. Los Angeles: Biomedical Simulations Resource, 1989, pp. 165-177. All four of these references are hereby incorporated by reference in their entirety. It has been discovered that the FOS process can be used for spectral analysis of quasi-periodic biological signals such as, but not limited to, ECG, respiratory function, pulse oximetry, perfusion data, and gamma Electroencephalogram (EEG) signals. The process can be used to create multiple unique 3D Phase Space plots for time series data such as ECG, respiratory rate, pulse oximetry, perfusion data and gamma EEG waves.

The FOS process creates a finite series, or sum, of weighted basis functions. The basis functions can be non-linear mathematical functions, in this case alternating sine and cosine functions that model the surface ECG as a finite series in which the sinusoidal frequencies are not necessarily integral multiples of a fundamental frequency. The FOS process can generate multiple sine and cosine term pairs to build an accurate model of the heart's electrophysiology. The FOS process can determine the values of the amplitude, frequency and phase of the sine and cosine basis functions by searching through a set of frequencies and calculates the amplitude for each term until there is no significant energy left in the signal. The square of the amplitude of the ECG signal is representative of the energy of the signal. Each term in the finite series created by FOS has amplitude. When all the terms are added together it may nearly duplicate the original ECG signal.

The FOS process creates models with terms that are highly correlated with the target ECG signals. In one alternative, the latest sine/cosine pair added to a model has the frequency chosen such that the added pair will cause the greatest reduction in the mean square error (MSE) of approximating the target ECG signal. The process can continue until there is no sine/cosine pair remaining that can cause a reduction in MSE exceeding a predetermined bottom threshold. The bottom threshold is selected in such a way that unwanted biological signals or 'random noise' that may be present in the ECG signal tend not to be fit by the developed model. This FOS alternative was used in the above-referenced 1989 article by Korenberg and Paarmann, the above-referenced 1994 article by Adeney and Korenberg, and the above-referenced 2001 article by Chon. However, in another alternative, modified FOS (MFOS), more than one sine/cosine pair may be added at the same time to the model. If Q denotes the reduction in MSE corresponding to a particular frequency for a sine/cosine pair, then choose the candidate frequency with largest Q value and all candidate frequencies occurring at "relative maxima" of Q that exceed a specified threshold level. Here a "relative maximum" of Q occurs at a candidate frequency $\omega$ if Q has a greater value at $\omega$ than at the candidate frequencies to the immediate left and right of $\omega$ (i.e., the candidate frequencies just less than or greater than $\omega$). This alternative both accelerates the MFOS model-building and helps MFOS approach a globally-optimal solution, in terms of MSE or certain other measures of approximating the signal. In some cases, the separation between candidate frequencies might not be sufficiently fine to make clear which candidate frequencies are at "relative maxima" of Q, or more generally in other applications it might not be possible or meaningful to choose candidates corresponding to "relative maxima" of Q. For example, there may be no logical ordering of the candidates as there is with candidate frequencies. Then rather than at each stage merely selecting the candidate with largest Q value, one may optionally select all candidates causing a reduction in MSE above a specified threshold level or, e.g., the 2 or 3 candidates causing the greatest reductions in MSE. Thus, MFOS is a general purpose model-building algorithm that can be used to select model terms from a wide variety of candidate types, including complex exponentials, hyperbolic functions, chirp signals, and delayed output and input terms and crossproducts thereof. Note that delayed output and input terms and crossproducts thereof can be logically ordered, and MFOS is well-suited to building nonlinear or linear difference equation models. Further details are provided in the Korenberg article (Biological Cybernetics 60:267-276, 1989), cited above.

As mentioned previously, FIG. 4A is a flow chart 74 depicting the steps of one embodiment of a modified fast orthogonal search (MFOS) process which may be used to produce a model-derived reconstruction of the ECG signal according to some of the embodiments disclosed herein. To begin with, at step 76, an ECG signal is received as input. The ECG signal can be represented as a time series for N number of samples in the data set.

At step 78, a functional expansion model to approximate the input ECG time series is created using implicitly created orthogonal functions. The obtained functional expansion includes an implicitly-created orthogonal function with an orthogonal weight BI and the expansion has a residual error E2. Normally, the implicitly-created orthogonal function is derived from a non-orthogonal candidate function using MFOS, based on a Gram-Schmidt (GS) orthogonalization process. At 80 MFOS chooses a candidate sine/cosine pair or pairs or other candidate term or terms causing the greatest (maximum) or relatively greatest (relative maximum) reduction of the mean square error (MSE) of approximating the input ECG time series. The orthogonal weights BI are calculated in such a manner that minimizes a mean square error (MSE) of the obtained functional expansion from the input ECG time series.

Thereafter at step 82, 84 and 86, the MFOS process may be stopped when at least one of the following predefined conditions are met. Firstly, an acceptably small residual MSE has been achieved. Secondly, the search may also stop when a certain number of terms have been fitted. (This parameter is referred to as maximum terms to add (mTTA)). Thirdly, the search may stop when none of the remaining candidates can yield a sufficient MSE reduction value. As a non-limiting example, one criterion in such an embodiment would be representative of not having any candidates that would yield an MSE reduction value greater than would be expected if the residual were white Gaussian noise. As another non-limiting example, in the above-referenced 1989 Korenberg article in Biological Cybernetics, to achieve accurate spectral estimation of narrow- and wide-band processes, a low threshold (0.2% of the time-series variance) was set as the minimum reduction in mean square error required before a further addition could be made to the model. As another non-limiting example, in the above-referenced 1989 Korenberg article in Biological Cybernetics, to attempt to recover a time-series as it existed prior to corruption by a noise process, a higher threshold (4% of the noisy time-series variance) was set as the minimum reduction in mean-square error required before a further addition could be made to the model.

At the final step 88, the weights AI of selected non-orthogonal candidate terms are calculated recursively using orthogonal weights BI. An important part of FOS and MFOS is that choosing the terms for the model includes the step of searching through one or more sets of candidate terms.

FIGS. 4B and 4C show the first-stage search results of applying MFOS to the same example as in the above-referenced 1989 article by Korenberg and Paarmann. The time series was formed by the sum of 5 sinusoidal signals, with radian frequencies 0.08, 0.10, 0.45, 0.60, and 0.85. In the article, 151 points of time-series data were used, but the same frequencies are found in the same order by FOS when 150 points are used here. Also, in FIGS. 4B and 4C, dimensionless time is assumed; if instead time was measured in seconds, then the candidates would have units rad/sec.

In the first test, there was no noise contamination, and the 0.2% threshold was used as one way to achieve accurate spectral estimation. FOS stopped after identifying the correct frequencies over 5 search stages, selecting one radian frequency per stage in this order: 0.60, 0.10, 0.45, 0.85, 0.08. The ordered pairs displayed near the peaks in FIG. 4B (and also in FIG. 4C) show the radian frequencies where the significant relative maxima of the MSE reduction occurred, plus the value of these maxima. For example the first significant relative maximum in FIG. 4B occurred at radian frequency 0.10, where the MSE reduction was 0.89. Here, MFOS was able to select the first 4 of the FOS-found frequencies in the first search stage (FIG. 4B), which left only the 0.08 radian frequency to be found in the second search stage. Hence MFOS significantly reduced the required run time, and provided equivalent accuracy to FOS.

Next, the time series was contaminated with additive zero-mean uncorrelated uniformly-distributed noise, with variance equal to that of the original time series, to create a noisy time series with SNR of unity (i.e., 0 dB, the 100% noise contamination case in FIG. 4C). As one attempt to recover the time-series as it existed prior to corruption by the noise, the 4% threshold was employed. FOS stopped after 4 search stages, selecting one radian frequency per stage in the order: 0.60, 0.09, 0.83, 0.45. The 0.08 radian frequency was missed. For the same number of selected frequencies, MFOS already did better in the first search stage: the 4 largest relative maxima in FIG. 4C occur at radian frequencies 0.10, 0.45, 0.60, 0.84. Hence here MFOS was both significantly faster and more accurate than FOS. In some cases MFOS can find all the model terms in the first search stage, in other cases it may require additional search stages, but it is generally much faster than FOS.

In this application, the FOS and MFOS methods are used to build a model approximating an electrophysiological signal. The FOS and MFOS methods include choosing a measure of approximating the signal. For example, the measure may be the mean square error (MSE), but could instead involve weighted MSE, or perpendicular distance to a hyperplane. The MFOS method involves a search through candidate terms to select terms to add to the model at successive stages, wherein at least two distinct candidate terms are selected at the same stage at least once, where one of the selected terms causes, out of the candidate terms searched, the greatest reduction in the measure of approximating the signal, and another of the selected terms is, out of the candidate terms searched, at a relative maximum of the reduction of the measure of approximating the signal. If there is no logical ordering of the candidates as there is with candidate frequencies then, at the same stage at least once, select two or more candidates causing a reduction in MSE above a specified threshold level.

The methods can be combined with least angle regression (LARS), by Efron, Hastie, Johnstone, and Tibshirani ("LEAST ANGLE REGRESSION", The Annals of Statistics, 2004, Vol. 32, No. 2, 407-499, 2004). Suppose that the candidates can be ordered (e.g. by the frequency ω of a sine/cosine pair or a complex exponential). LARS begins by finding the candidate function $x_j$ with which the desired response y is most correlated, and adds this candidate to the model. One extension is to also choose other candidates whose correlation with y is at a relative maximum, but for simplicity assume that only $x_j$ is chosen. The residual is $y-kx_j$ where the coefficient k is increased in the direction of the sign of the correlation of $x_j$ with y until one of the other candidates, say $x_i$, has as much correlation with the current residual as does $x_j$. For simplicity, assume that the candidates are positively correlated with the current residual; if not true for a particular candidate replace it by its negative (sometimes called the reversed covariate). The candidate $x_i$, corresponding to the smallest positive value of k, is then added to the model. As a second extension, one can also add other candidates corresponding to one or more relative minima of k.

Figure 5:
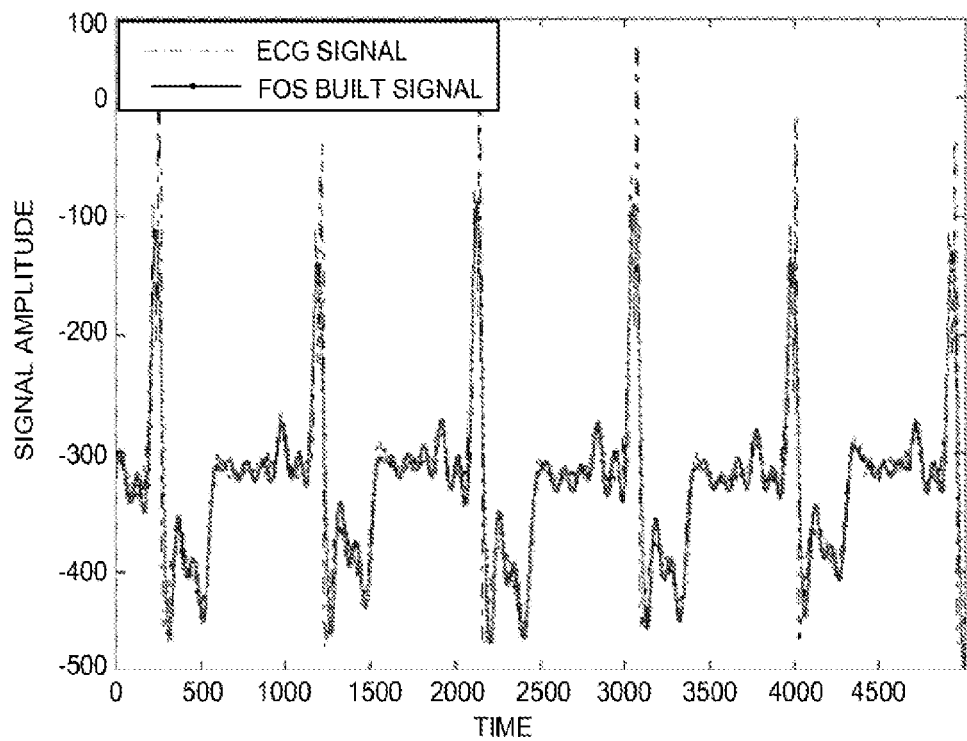
FIG. 5 shows an ECG waveform from patient data vs. a FOS reconstructed ECG waveform using twenty sine/cosine pairs of basis functions, for the first 5000 time points in accordance with an embodiment of the claimed invention.
Figure 6:
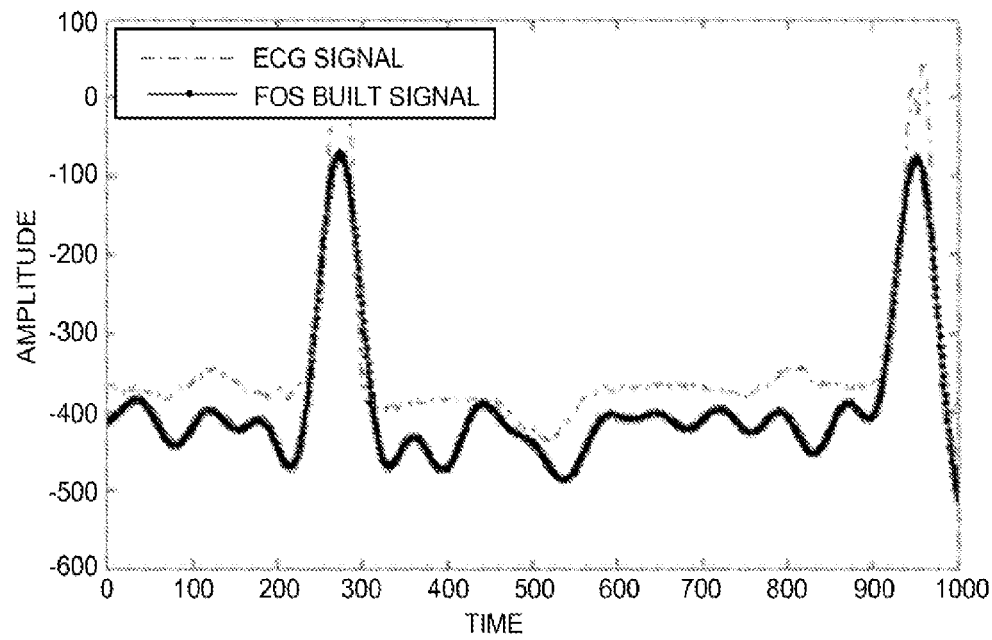
FIG. 6 shows a FOS reconstructed ECG waveform using twenty sine/cosine pairs of basis functions, for the first 1000 time points in accordance with an embodiment of the claimed invention.
Figure 7:
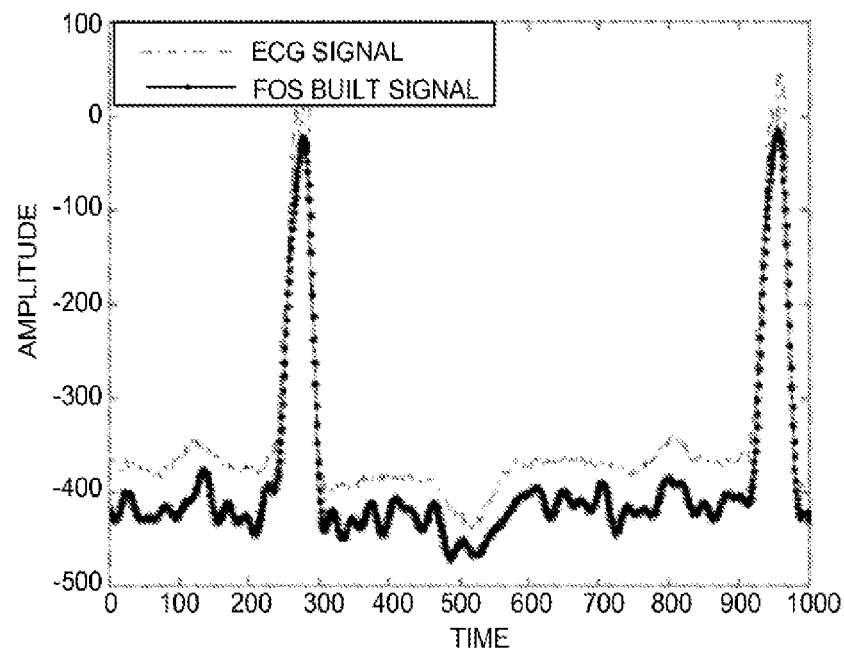
FIG. 7 shows a FOS reconstructed ECG waveform using fifty sine/cosine pairs of basis functions in accordance with an embodiment of the claimed invention.
Figure 8:
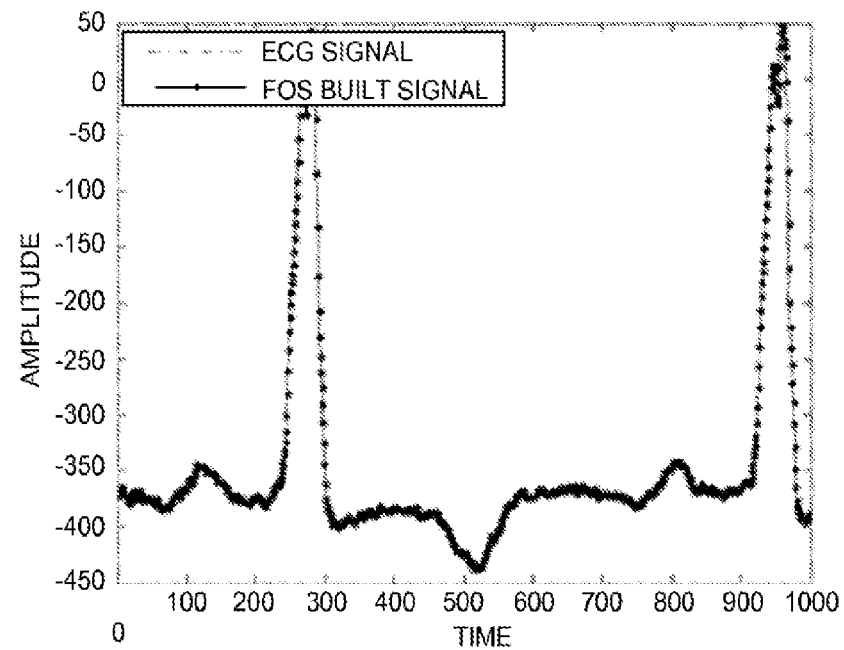
FIG. 8 shows a FOS reconstructed ECG waveform using one hundred sine/cosine pairs of basis functions in accordance with an embodiment of the claimed invention.

FIGS. 5-8 show the typical ECG time series data modeled at different resolutions by FOS by changing the maximum number of terms parameter. The addition of sinusoids without enough terms lacks the resolution to model the original signal with high fidelity. A normal FOS reconstructed ECG is shown in FIG. 5. The FOS reconstructed ECG using twenty sine/cosine pairs of basis function terms producing a compression ratio of 33:1 and Mean square error of 4.39 is shown in FIG. 6. The FOS reconstructed ECG using fifty sine/cosine pairs of basis function terms producing a compression ratio of 13:1 and MSE of 4.38 as shown in FIG. 7. The FOS reconstructed ECG using one hundred sine/cosine pairs of basis function terms producing a compression ratio of 10:1, and the MSE reduced to the order of $10^{-7}$ is shown in FIG. 8. Thus a higher resolution can be accomplished by using more basis functions.

Figure 9:
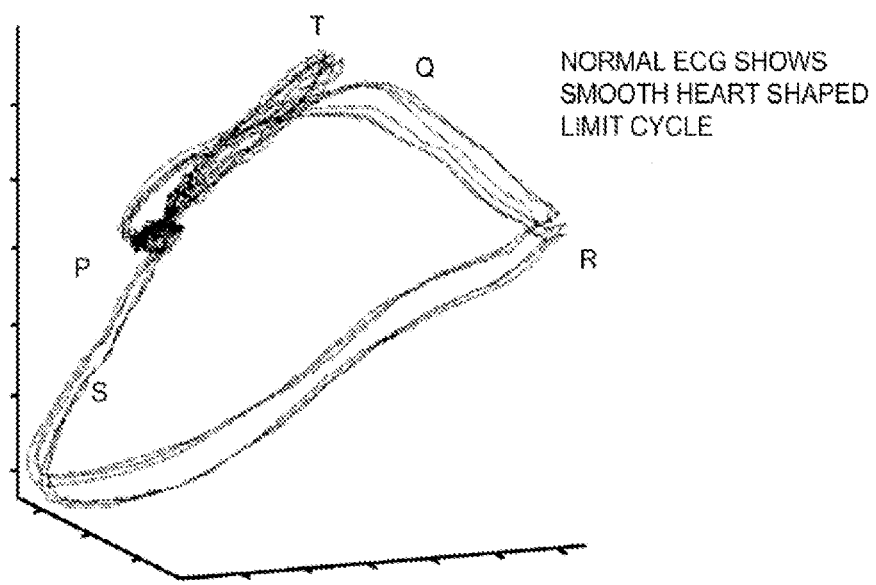
FIG. 9 shows a normalized Phase Space Portrait of an orthogonal lead ECG after applying a fast orthogonal search reconstruction in accordance with an embodiment of the claimed invention.

FIG. 9 is a phase space plot representing the ECG signal in accordance with an embodiment of the invention. The phase space plot includes a vector space (called a state space or phase space) for the system such that specifying a point in this space specifies the state of the system at a specific time, and vice versa. The dynamics of the system can be interpreted easily now by studying the dynamics of the corresponding phase space points. In theory, dynamic systems are usually defined by a set of ordinary differential equations acting on a phase space. Since the human heart ECG signals can be considered a non-linear dynamic system, therefore to represent ECG signals in the phase space, FOS is used to convert a dynamic system into state space and generate a geometrical manifold. The smooth heart shaped limit cycle of the normal ECG in the form of a P-Q-R-S-T waveform can be seen in FIG. 9. This ECG based manifold can be generated by using the spectral FOS or MFOS by reconstructing the signal using the non-linear terms to rebuild and plot the 3D trajectory in phase space which resembles a 3D vector cardiogram.

Figure 10:
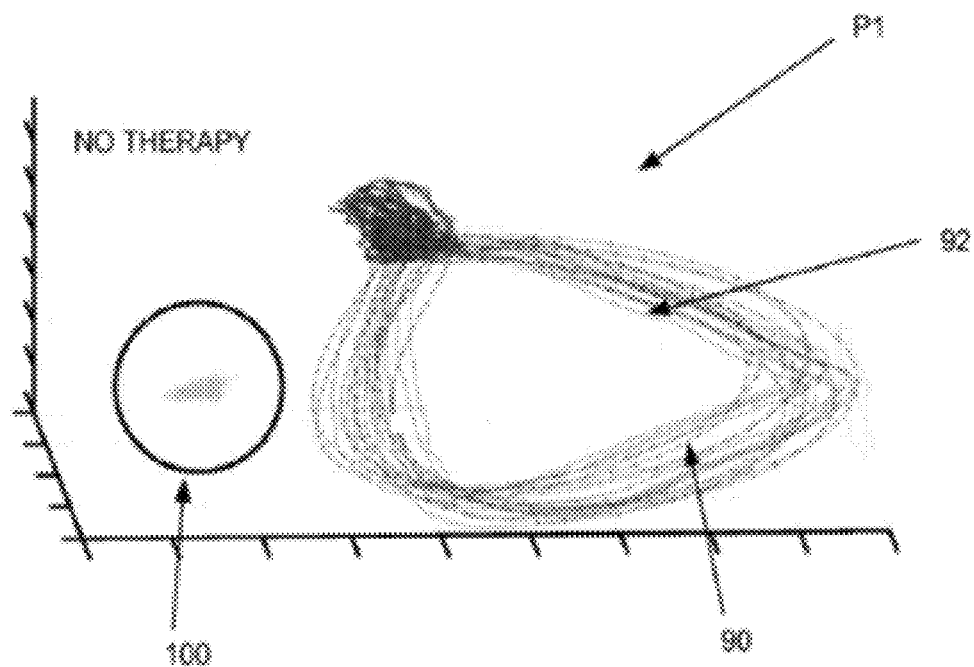
FIG. 10 shows a three-dimensional phase space plot in accordance with an embodiment of the claimed invention representative of a patient's heart without ventricular arrhythmia over a mean three year follow up.
Figure 11:
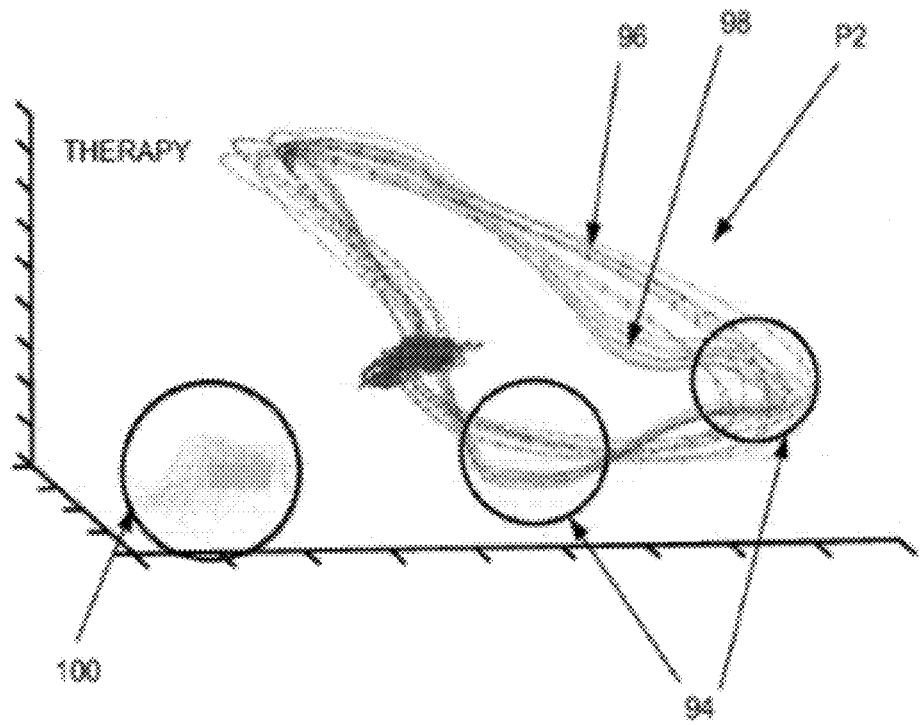
FIG. 11 shows a 3D phase space plot in accordance with an embodiment of the claimed invention representative of a patient's heart with some kind of arrhythmia.

FIGS. 10-11 show the three dimensional (3D) phase space plot of the patient's ECG. FIG. 10 is a representative phase space plot P1 of an implantable cardioverter defibrillator (ICD) recipient without ventricular arrhythmia over a mean three year follow up. The phase space plot P1 includes a plurality of dotted trajectories 90 and a plurality of non-dotted trajectories 92. The dotted trajectories 90 represent a modeled normal conduction path without complex sub-harmonic frequencies (CSF). The non-dotted trajectories 92 represent the actual conduction path of the patient's heart. FIG. 11 is another phase space plot P2 representative of another patient that received appropriate ICD therapy. The conduction delays 94 can be read from the phase space plots as illustrated for P2. (A similar determination could be made for P1). The departure between the dotted trajectories 96 and the non-dotted trajectories 98 can be interpreted as the conduction delays 94, which may be due to abrupt changes in impedance that are responsible for the generation of complex sub-harmonic frequencies. The intersection of the dotted trajectories 96 and the non-dotted trajectories 98 mark the regions showing conduction delays 94.

Although this embodiment uses dotted and non-dotted lines to show the trajectories, other embodiments may use other marking methods to tell the two types of trajectories apart. Other marking methods may include, but are not limited to methods that are discernible from one another in a black and white (monochrome scenario) or methods which color the different trajectories differently.

A circled subspace 100 in FIGS. 10-11 represents the 3D trajectory magnitude and orientation of complex sub-harmonic frequencies (CSF). The circled subspace 100 is the 3D phase space representation of a spectrum of the complex sub-harmonic frequencies. These CSF trajectory subspaces are hidden in the ECG signals. The CSF represents abnormal conduction related to a pathological process in the heart. Normally, low energy components in the output of FOS are associated with the pathological process. There are a variety of pathological processes which can affect the patient's ECG. Such pathological processes can lead to either atrial or ventricular arrhythmias. We subsequently describe the example of FOS analysis assessing ventricular arrhythmia risk: After applying FOS to the ECG, the FOS generates incongruency in the dotted trajectories 96 and the non-dotted trajectories 98. This incongruency can be quantified in the form of the subspace 100.

To model the ECG signal it is helpful to determine the behaviour of the ECG signal. In some embodiments, the Lyapunov exponents can be used to describe the behavior of dynamical systems. Lyapunov exponents tell us the rate of divergence of nearby trajectories, a key component of chaotic dynamics. The Lyapunov exponent measures the average rate of the divergence or convergence of orbits starting from nearby initial points. Therefore, the Lyapunov exponent can be used to analyze the stability of limit cycles and to check for sensitive dependence on initial conditions, that is, the presence of chaotic attractors. This can be done in some embodiments by computing Lyapunov spectra with a continuous FOS or MFOS based Gram Schmidt orthogonalization process. Such a process may be used as a secondary predictor by calculating the change and mean Lyapunov exponent to predict arrhythmias.

The FOS- or MFOS-derived signal is a linear combination of certain well behaved signals such as sinusoidal signals and/or exponentially-decaying sinusoids that can be noiselessly differentiated. The resulting derivative is also a FOS-derived signal and can again be noiselessly differentiated, and so on. This contrasts with other procedures where the model output cannot be differentiated noiselessly. In some embodiments, if one compares the ratio of the derivative of the FOS- or MFOS-derived signal with the original signal, one can get a measure in some respects similar to the Lyapunov exponent. If the ratio is positive, then the signal will have growing amplitude indicating instability. If the ratio is negative, then the signal will have decreasing amplitude. In some embodiments, by following the value of the ratio, it can be determined when the signal is growing in amplitude, or oscillating with increasing amplitude. Similarly, in other embodiments, by following the value of the ratio of the second derivative with the first derivative, it can be determined when the first derivative is increasing in amplitude, and may be helpful in predicting arrhythmias in various locations in the heart.

In some ECG-related embodiments, a color coded scale can be used to indicate the present status of the heart in a diagram. As one non-limiting example, the ratios can be displayed using a red-green continuum, where the more positive the ratio the more intensely red is the color, and the more negative the ratio the more intensely green is the color. The positive value of the ratio can be assigned a red color. The negative value of the ratio can be assigned a green color. The positive value of the ratio can be considered as a danger sign for the patient. In contrast, the negative value of the ratio can be considered as a safer sign for the patient. Every point on the vectrocardiogram represents a particular location of the heart of the patient. Thus, the green and red colors on the vectrocardiogram for such an embodiment could represent the current status of the patient.

Another embodiment of the present disclosure is to build FOS or MFOS models whereby the pathological event identified is a prediction of a clinical outcome or diagnosis, e.g. sudden cardiac death, atrial or ventricular fibrillation, death/survival. For embodiments examining ECG signals, the FOS model terms may be selected from candidate terms such as R interval, QT interval, ST segment, a QRS complex interval, heart rate, amplitude or shape or duration of the T wave, PR interval, amplitude or shape or duration of the P wave, a direction of a significant axis determined by principal component analysis, various measures of conduction delays, the entire complex from P wave to T wave, ejection fraction, other measures of cardiac function, and cross-products thereof. Depending on the order of cross-product terms, there may be thousands or millions of candidate terms, but FOS or MFOS can build a concise model with unobvious terms that are good indicators of clinical outcome or diagnosis. A huge advantage of this approach is that it enables using together many different previously proposed indicators of cardiac function and making new predictors by FOS- or MFOS-selected combinations and cross-products of existing indicators.

It should be appreciated that the stability of the system can also be checked using the stability ratio in desired embodiments. The stability ratio can also perform a similar purpose as the Lyapunov exponent. The stability ratio needs the output from the FOS or MFOS model. The stability ratio is derivable from a model when the output is differentiable. However, the Lyapunov exponent can be calculated without using the output from the FOS model. It should be appreciated that, although the output of a FOS model is not essential, one can get a more accurate estimate of the Lyapunov exponent if the output of the FOS or MFOS model is available. The Lyapunov exponent can be calculated even before the calculation of the FOS model so it can be done on a much longer record.

There are two ways the Lyapunov exponent can be calculated. One method uses output from the FOS model, while the other method does not use the FOS model to calculate the Lyapunov exponent. The Lyapunov exponent can be measured throughout the limit cycle.

According to an embodiment of the disclosure, the Lyapunov exponent can be calculated separately for the ventricles and the atrium. For the ventricle, the R wave of the ECG signal is detected and at that point the average is calculated. Once the average is calculated, a baseline reference can be calculated. Whenever the Lyapunov exponent goes above the baseline reference, it will indicate the stability of the system. In other words, it indicates that particular region of the ventricles is fine. Similarly for atrium, the P wave is detected in the system and the Lyapunov exponent is calculated for P wave. In the next step, the average is measured and checked for how long it stays positive. This can be evaluated to the entire limit cycle. Every point on the limit cycle can have three hundred Lyapunov exponents and within each point while moving along the limit cycle, it can be checked whether the system is moving towards stability or instability.

It should be appreciated that the stability ratio can also be applied at the different type of subspaces like the low energy terms and the complex sub-harmonic frequency. While calculating the stability ratio, not only the ratio of first derivative and base function (Y'/Y) but the ratio of second derivative and first derivative (Y''/Y') is also very important, especially when one tries to detect arrhythmias like tachycardia. In case of tachycardia, Y''/Y' would be very sensitive to increase in the first derivative. It can be determined when the first derivative is increasing in amplitude, and this is useful in predicting tachycardia in various locations in the heart.

The low energy term can be selected after certain terms. In one illustrative embodiment, the last 20% of the terms can be chosen, while in another embodiment, the last one hundred terms can be taken as the low energy terms. Other embodiments may use higher or lower percentages of the terms as the low energy terms or less than or more than 100 terms as the low energy terms. These chosen last few terms should be picked to contain a lot of the hidden low energy signal dynamics. We can noiselessly find the derivative of these components, since it is a linear combination of sine and cosine terms.

According to an embodiment of the disclosure, the method can also be used to build the three dimensional (3D) model of the heart. This method involves preparing a 3D phase space diagram using the ECG and superimposing the 3D phase space diagram on a 3D outline of a heart so that one can show where the damaged area is present on or within the heart. It should be appreciated that the heart can be cut and sliced to show the various regions to provide a 3D mesh of the whole heart. This is digital reconstruction of the ECG of the heart showing Epicardium, Endocaridum and all this based on a three orthogonal lead ECG. The traditional method uses a combination of CT scan, and approximately two hundred electrodes from top to bottom. They register a frame and use electrodes to generate a voltage gradient map. The present invention makes use of only three electrodes and provides details of the heart non-invasively. Thus it is inexpensive.

It is always helpful for a doctor to detect the early damage in the heart. The current method generates the 3D model of the heart with high speed and uses the electrical conduction of the heart. The traditional method uses Magnetic resonance imaging (MRI) or Computed Tomography (CT) for the diagnostic imaging of the heart to analyze the damaged area in the heart. The MRI uses a contrast agent to enable the user to view the contrast image of the damaged tissue within the heart. The damaged tissue will absorb more contrast agent, which will identify the region of the dead tissue. If there are multiple regions with dead tissue, then it is not possible to determine which region specifically is causing instability in the heart using MRI. MRI cannot determine the electrical source of damage in the heart. In contrast, the current method uses the electrical conduction of the heart to generate a 3D model of the heart. Thus, it helps in determining the location of the tissue causing instability. The current method can also be used in other conditions when there is no structural instability such as abnormal blood flow.

It should be appreciated that the twelve lead ECG can be transformed in to the three lead vectrocardiogram (VCG) or vice versa using a FOS or MFOS or parallel cascade identification (PCI) model. To identify such models, training data can be used where both the twelve lead ECG and the three lead VCG have been simultaneously recorded. Then FOS, MFOS, and PCI models can be identified when the twelve lead ECG signals are the training inputs and the three lead VCG signals are the desired outputs, resulting in models that can transform twelve lead ECG into approximately three lead VCG. Alternatively, FOS, MFOS, and PCI models can be identified when the three lead VCG signals are the training inputs and the twelve lead ECG signals are the desired outputs, resulting in models that can transform three lead VCG into approximately twelve lead ECG. The VCG uses 3 channels connected in a orthogonal lead arrangement. It should also be appreciated that the transform of twelve-lead ECG signal to three-lead vectorcardiography or a reverse transform of three-lead vectorcardiography to twelve-lead ECG can be done by either using FOS, MFOS, or PCI. Traditionally, the methods use processes like Karhunen-Loeve, Dower, and Levkov to convert the VCG to ECG and vice versa. FOS- and MFOS-based transformations provides efficient compression, white noise removal, and removal of baseline drift with conversion of ECG into a vectorcardiogram, or vice versa. Also, while the VCG 3 channels are meant to be an orthogonal arrangement, the Gram-Schmidt or another orthogonalization process can be used to create, from portions of the three lead VCG signals, 3 orthonormal signals, i.e. 3 signals that actually are mutually orthogonal, each of which have unity mean-square. These orthonormal signals can be used in place of the portions of the three lead VCG signals, and can enhance the accuracy of the obtained results. A similar orthogonalization procedure can be applied using portions of some or all of the twelve lead ECG signals.

According to another embodiment of the invention, the FOS and MFOS processes can also be used for the purposes of a stress test since this form of testing is a well-established means of detecting underlying ischemic heart disease. The patient will have their heart rate increased (i.e. stressed) by either exercise or pharmaceutically. In some embodiments, the methods disclosed herein may also be used to identify underlying ischemic heart disease without the need to put the patient under stress conditions, thereby avoiding putting such patients at higher risk with a stress test. As with the previous methodology, a high resolution ECG will be obtained at increasing heart rates including peak heart rate. These data will then be assessed as per the previously described methodology.

According to yet another embodiment of the disclosure, the FOS and MFOS generated subspaces can also be used to extract the fetal ECG from an ECG recorded on the mother's abdomen. The process for extracting the fetal ECG consists of two steps: first, the ECG of the fetus is extracted from the original signal using a 3D FOS transform. Maternal ECG represents the remaining subspace energy.

According to still another embodiment of the disclosure, the FOS or the MFOS process can also be used to calculate the heart rate variability. The brain is linked to the autonomic nervous system which, amongst many systems in the body, controls heart rate and cardiac output. Heart rate variability analysis traditionally requires observing variability of the R-R interval. Fast orthogonal search (FOS) and modified fast orthogonal search (MFOS) can be used to model the entire signal 3D ECG data and this can be used to generate other subspaces of the 3D ECG signal which can replace traditional variability analysis. These subspaces are linked to specific properties of parallel cascades of non-linear systems and as such can be used to model the states of the brain and the heart. More specifically, this invention is a method and associated apparatus for evaluating electrophysiological signals in a manner that will sensitively and specifically predict current and future pathological events such as heart disease, diabetic autonomic neuropathy, cardiac arrhythmias, Parkinson's disease, epilepsy, brain injury/disorders and altered states of cognition such as bipolar disorder and attention deficit disorder (ADD).

According to still another embodiment of the invention, the method is also used as a tool to track severity of illness in critically ill patients in the ICU (Intensive Care Unit). The combination of FOS (or MFOS) and 3D phase space plot offers a potential opportunity to quantify severity of illness, thereby determining if patients are improving or deteriorating during a longer period of time. The FOS or the MFOS process produces a multidimensional formula for the ECG time series of any given length. This formula describes a dynamic system given by a set of real numbers (a vector) which can be represented by a point in an appropriate phase space. Small changes in the state of the system correspond to small changes in the set of real numbers such that a point in space becomes a point in time in the 3D ECG signal. For a given time interval only one future state follows from the current state. This is the dynamic systems approach which is used to generate the differential equations that model the dynamic system of the heart. This dynamic model has the potential to model the heart's stability at different heart rates and to simulate the effectiveness of cardio-active medications. This method allows for accurate prediction of arrhythmias (Atrial Fibrillation/Ventricular Fibrillation/Ventricular Tachycardia) that may lead to sudden cardiac death of the patient.

In other advantages of this particular invention, the biological noise during inhalation and exhalation, and external noise from communication devices, switching power supplies and terrestrial power lines, can be detected and excluded or attenuated by customizing FOS or MFOS.

Figure 12:
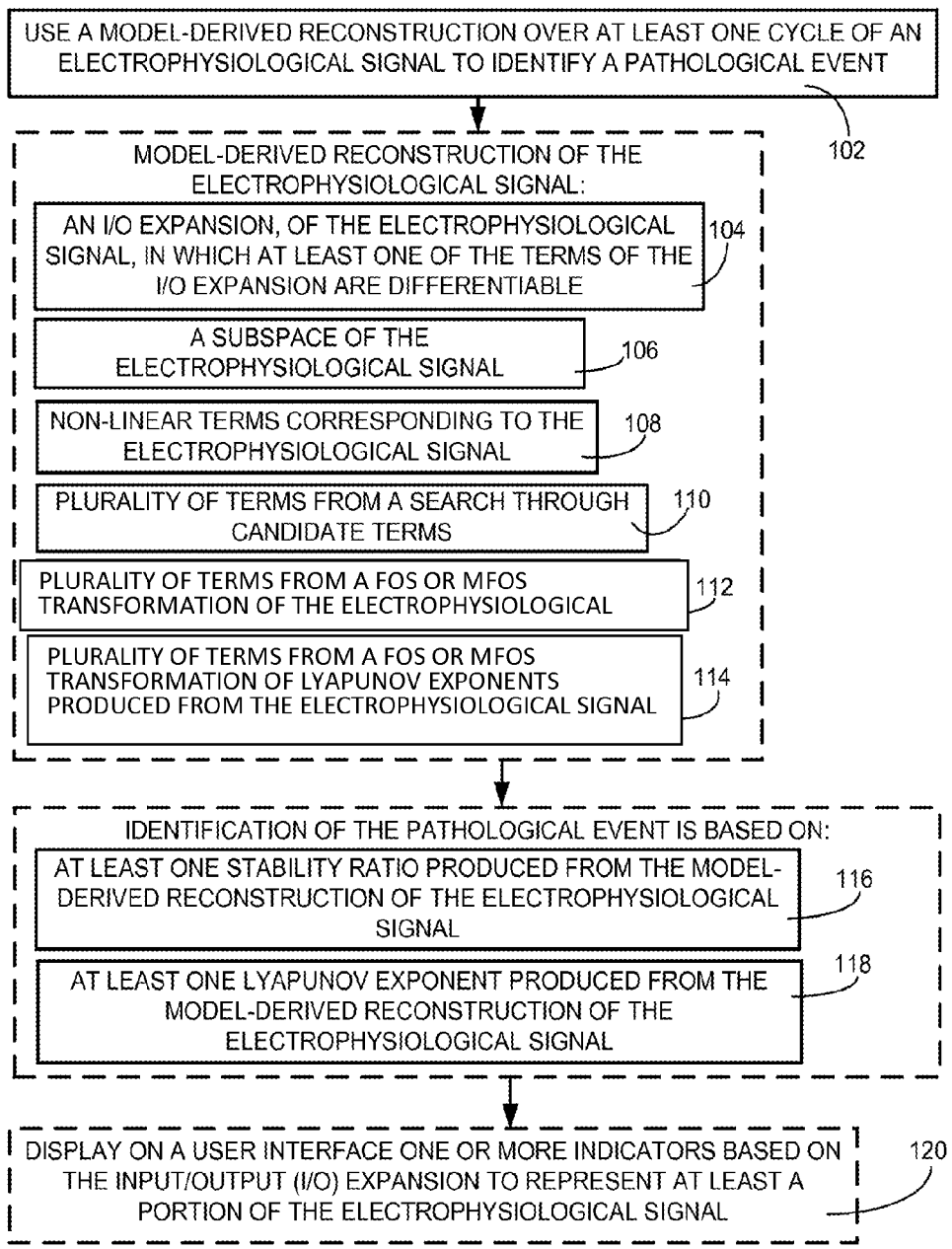
FIGS. 12-14 illustrate different embodiments of a method for evaluating an electrophysiological signal.
Figure 13:
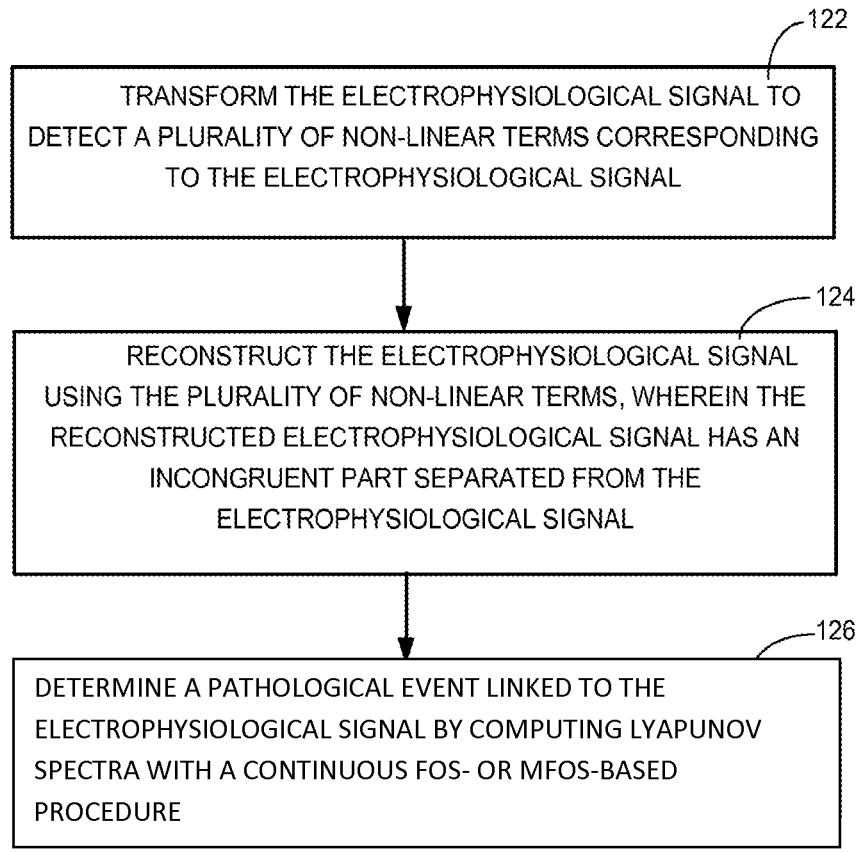
Figure 14:
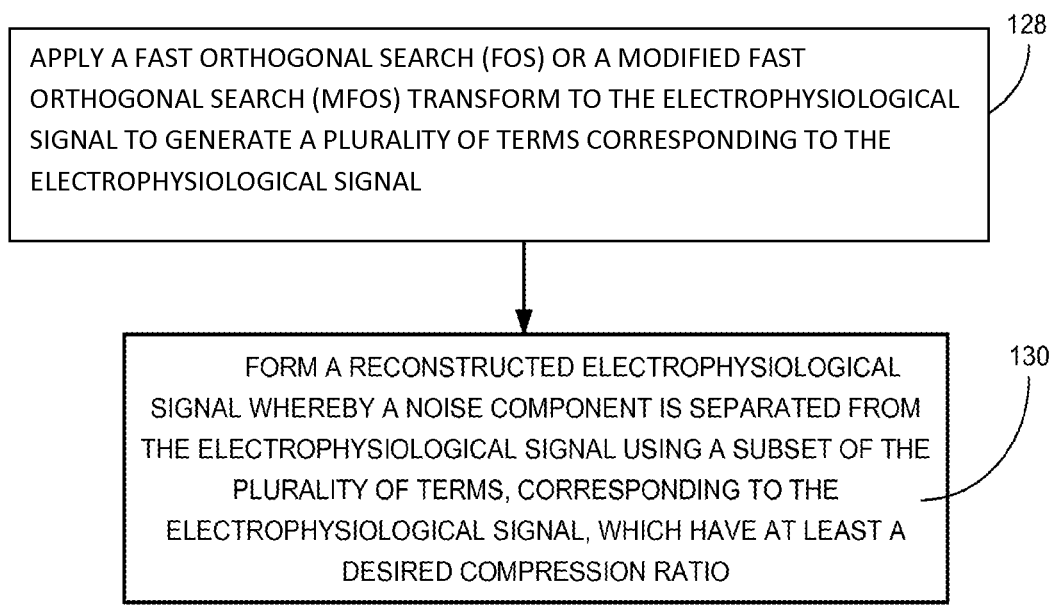

FIGS. 12-14 illustrate different embodiments of a method for evaluating an electrophysiological signal. In FIG. 12, a model-derived reconstruction over at least one cycle of the electrophysiological signal is used 102 to identify a pathological event. Examples of electrophysiological signals include, but are not limited to an electrocardiogram (ECG), an electroencephalogram (EEG), a gamma synchrony signal; a respiratory function signal; a pulse oximetry signal; a perfusion data signal; a quasi-periodic biological signal; a fetal ECG; a blood pressure signal; and a heart rate signal. Examples of a pathological event which may be identified include, but are not limited to a heart disease, a cardiac arrhythmia, a diabetic autonomic neuropathy, Parkinson's disease, a form of epilepsy, a brain injury, an altered state of cognition, a stability of a heart at different heart rates, an effectiveness of a medication, an escemia, a silent eschemia, an atrial fibrillation, a ventricular fibrillation, a ventricular tachycardia, a blood vessel block, attention deficit disorder, and pulsus paradoxus.

The model-derived reconstruction of the electrophysiological signal may comprise various elements, depending on the embodiment. For example, in some embodiments, the model-derived reconstruction of the electrophysiological signal comprises 104 an input/output (I/O) expansion, of the electrophysiological signal, in which at least one of the terms of the I/O expansion are differentiable. In some embodiments, at least one term of the I/O expansion that is differentiable is analytically differentiable. In other embodiments, the I/O expansion may comprise a ratio comprising a derivative of the model-derived reconstruction. In still further embodiments, the I/O expansion may comprise a ratio of a first derivative of the model-derived reconstruction of the electrophysiological signal to the model-derived reconstruction of the electrophysiological signal. In still other embodiments, the I/O expansion may comprise a ratio of a second derivative of the model-derived reconstruction of the electrophysiological signal to a first derivative of the model-derived reconstruction of the electrophysiological signal.

In other embodiments, the model-derived reconstruction of the electrophysiological signal may comprise 106 a subspace of the electrophysiological signal. The subspace of the electrophysiological signal may be selected to remove one or more complex subharmonic frequencies from the electrophysiological signal.

In other embodiments, the model-derived reconstruction of the electrophysiological signal may comprise 108 non-linear terms corresponding to the electrophysiological signal. In further embodiments, the model-derived reconstruction of the electrophysiological signal may comprise 110 a plurality of terms from a search through candidate terms. In still other embodiments, the model-derived reconstruction of the electrophysiological signal may comprise 112 a plurality of terms from a fast orthogonal search (FOS) transformation of the electrophysiological signal. For other embodiments, the model-derived reconstruction of the electrophysiological signal may comprise 114 a plurality of terms from a fast orthogonal search (FOS) transformation of Lyapunov exponents produced from the electrophysiological signal.

In other embodiments, the model-derived reconstruction of the electrophysiological signal may comprise terms from a model selected from the group consisting of an orthogonal search method, a neural network method, a genetic analysis method, a non-linear system identification method, and a method of searching through candidate terms.

In further embodiments, the model-derived reconstruction of the electrophysiological signal may comprise terms selected from the group consisting of sinusoidal terms, cosinusoidal terms, exponentially decaying sinusoidal terms, hyperbolic terms, exponential terms, chirp signals, and analytical solutions of differential equations.

Still referring to FIG. 12, in some embodiments, the identification of the pathological event may be based 116 on at least one stability ratio produced from the model-derived reconstruction of the electrophysiological signal. The at least one stability ratio may comprise a subspace derivative ratio. In other embodiments, the identification of the pathological event may be based 118 on at least one Lyapunov exponent produced from the model-derived reconstruction of the electrophysiological signal.

In some embodiments, the method for evaluating an electrophysiological signal may also include a step 120 of displaying on a user interface one or more indicators based on the input/output (I/O) expansion to represent at least a portion of the electrophysiological signal. For embodiments which have a model-derived reconstruction which is not based on an I/O expansion, the user interface may be used to display one or more indicators based on the model-derived reconstruction of the electrophysiological signal.

In some embodiments, the one or more indicators may be displayed on a phase space plot. In other embodiments, the one or more indicators may be displayed on at least a portion of the electrophysiological signal. In still other embodiments, the one or more indicators may be highlighted to further convey information about the pathological event identified from the model-derived reconstruction of the electrophysiological signal. The highlighted indicators may comprise color coded indicators, shaded indicators, one or more type of broken lines, and/or one or more type of line thicknesses.

In some embodiments, the one or more indicators may be displayed on a physiological image corresponding to the electrophysiological signal. Depending on the embodiment, the electrophysiological signal may comprise an electrocardiogram (ECG) and the physiological image may comprise an image of at least a portion of a heart and/or at least a portion of a circulatory system. In other embodiments, the electrophysiological signal may comprise an electroencephalogram (EEG) and the physiological image may comprise an image of at least a portion of a brain.

In further embodiments, the physiological image may comprise a two-dimensional image, a three-dimensional image, a time changing image (for example, a video, or time lapsed set of images at equal or non-equal intervals), a tissue model, or a tissue image from an actual subject from whom the electrophysiological signal was obtained.

FIG. 13 illustrates another embodiment of a method for evaluating an electrophysiological signal. The electrophysiological signal is transformed 122 to detect a plurality of non-linear terms corresponding to the electrophysiological signal. The electrophysiological signal is reconstructed 124 using the plurality of non-linear terms, wherein the reconstructed electrophysiological signal has an incongruent part separated from the electrophysiological signal. A pathological event linked to the electrophysiological signal is determined 126 by computing Lyapunov spectra with a continuous fast orthogonal search based Gram Schmidt orthogonalization. In some embodiments, a portion of the incongruent part of the electrophysiological signal may comprise a complex sub-harmonic frequency indicative of the pathological event. In other embodiments, the pathological event may comprise an abnormal conduction related to a pathological process in a patient's heart, and a relative orientation and a vector magnitude of the complex subharmonic frequency may comprise a risk stratifier for sudden cardiac death.

FIG. 14 illustrates another embodiment of a method of evaluating an electophysio logical signal. A fast orthogonal search (FOS) transform is applied 128 to the electrophysiological signal to generate a plurality of terms corresponding to the electrophysiological signal. A reconstructed electrophysiological signal is formed 130 whereby a noise component is separated from the electrophysiological signal using a subset of the plurality of terms, corresponding to the electrophysiological signal, which have at least a desired compression ratio. In some embodiments, a desired compression ratio is about 30 to 1, however higher or lower compression ratios may be desirable in other embodiments.

In further embodiments, the electrophysiological signal may comprise an electrocardiogram (ECG) signal, and the method may further comprise transforming the ECG signal into a vectrocardiogram. In other embodiments, the electrophysiological signal may comprise an electrocardiogram (ECG) signal from a mother's abdomen, and the method may further comprise extracting a fetus ECG from the mother's abdomen ECG using an FOS transformation.

Figure 15:
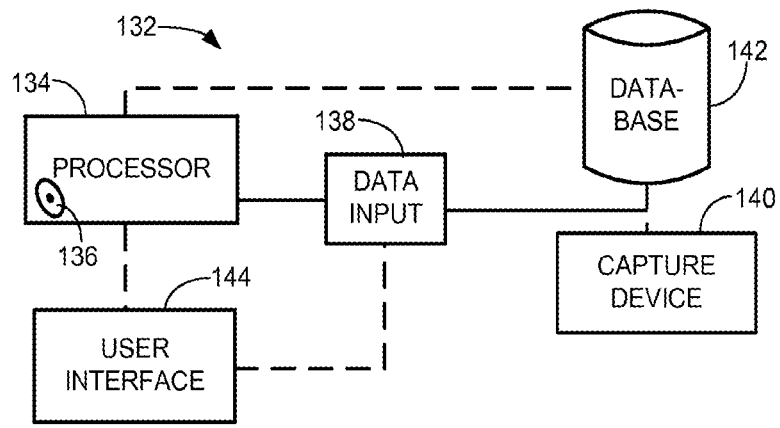
FIGS. 15-18 schematically illustrate different embodiments of a system for evaluating an electrophysiological signal.

FIG. 15 schematically illustrates an embodiment of a system 132 for evaluation of an electrophysiological signal. The system 132 has a processor 134 which is configured to identify a pathological event from a model-derived reconstruction of the electrophysiological signal. Embodiments of suitable processes and method steps to make this identification have already been discussed above. The processor 134 may be a computer executing machine readable instructions which are stored on a non-transitory computer readable medium 136, such as, but not limited to a CD, a magnetic tape, an optical drive, a DVD, a hard drive, a flash drive, a memory card, a memory chip, or any other non-transitory computer readable medium. The processor 134 may alternatively or additionally include a laptop, a microprocessor, an application-specific integrated circuit (ASIC), programmable logic array, digital circuitry, analog circuitry, or any combination and/or plurality thereof. The processor 134 may be a stand-alone unit, or it may be a distributed set of devices.

A data input 138 is coupled to the processor 134 and configured to provide the processor 134 with the electrophysiological signal. An electrophysiological signal capture device 140 may optionally be coupled to the data input 138 to enable the live capture of the electrophysiological signal. Examples of electrophysiological signal capture devices include, but are not limited to an electrocardiogram Holier monitor; a twelve lead electrocardiogram monitor; an eight lead electrocardiogram monitor; an electrocardiogram monitor using a bipolar lead system, an electrocardiogram monitor using a unipolar lead system, a brain computer interface (BCI), a mind machine interface (MMI), a direct neural interface, a brain machine interface, a profusion blood oxygenation sensor, a blood pressure sensor, a breathing rate sensor, and a fetal electrocardiogram monitor. Similarly, a database 142 may optionally be coupled to the data input 138 to provide a previously captured electrophysiological signal to the processor 134. Database 142 can be as simple as a memory device holding raw data or formatted files, or database 142 can be a complex relational database. Depending on the embodiment, none, one, or multiple databases 142 and/or electrophysiological signal capture devices 140 may be coupled to the data input 138. The electrophysiological signal capture device 140 may be coupled to the data input 138 by a wired connection, an optical connection, or by a wireless connection. Suitable examples of wireless connections may include, but are not limited to, RF connections using an 802.1 lx protocol or the Bluetooth® protocol. The electrophysiological signal capture device 140 may be configured to transmit data to the data input 138 only during times which do not interfere with data measurement times of the electrophysiological signal capture device 140. If interference between wireless transmission and the measurements being taken is not an issue, then transmission can occur at any desired time. Furthermore, in embodiments having a database 142, the processor 134 may be coupled to the database 142 for storing results or accessing data by bypassing the data input 138.

The system 132 also has a user interface 144 which may be coupled to either the processor 134 and/or the data input 138. The user interface 144 can be configured to display the one or more indicators discussed above. The user interface 144 may also be configured to allow a user to select electrophysiological signal data from a database 142 coupled to the data input 138, or to start and stop collecting data from an electrophysiological signal capture device 140 which is coupled to the data input 138.

Figure 16:
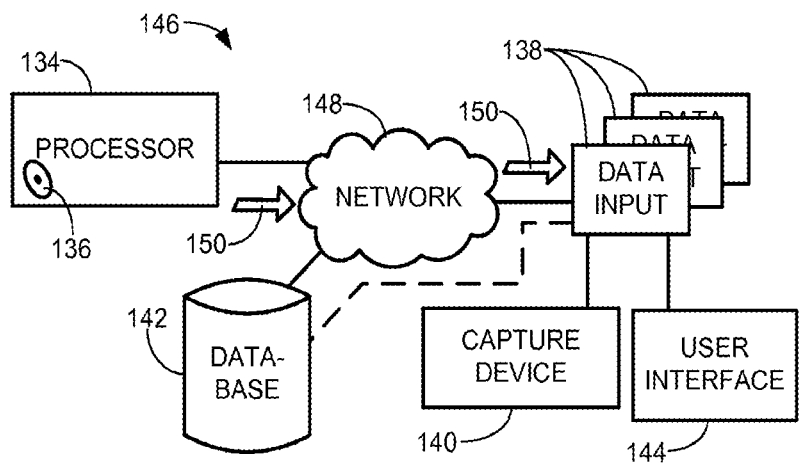

FIG. 16 schematically illustrates another embodiment of a system 146 for evaluating an electrophysiological signal. In this embodiment, the processor 134 is set-up to be a remote processor which is coupled to the data input 138 over a network 148. The network 148 may be a wired or wireless local area network (LAN or WLAN) or the network 148 may be a wired or wireless wide area network (WAN, WW AN) using any number of communication protocols to pass data back and forth. Having a system 146 where the processor 134 is located remotely allows multiple client side data inputs 138 to share the resources of the processor 134. Electrophysiological signals may be obtained by the data input 138 from a database 142 and/or an electrophysiological signal capture device 140 under the control of a user interface 144 coupled to the data input 138. The electrophysiological signal may then be transferred over the network 148 to the processor 134 which can then identify a pathological event from a model-derived reconstruction of the electrophysiological signal (as described previously) and transmit data signals 150 having the identified pathological event to the client side. Such data transmissions may take place over a variety of transmission media, such as wired cable, optical cable, and air. In this embodiment, the remote processor 134 can be used to help keep the cost of the client-side hardware down, and can facilitate any upgrades to the processor or the instructions being carried out by the processor, since there is a central upgrade point.

Figure 17:
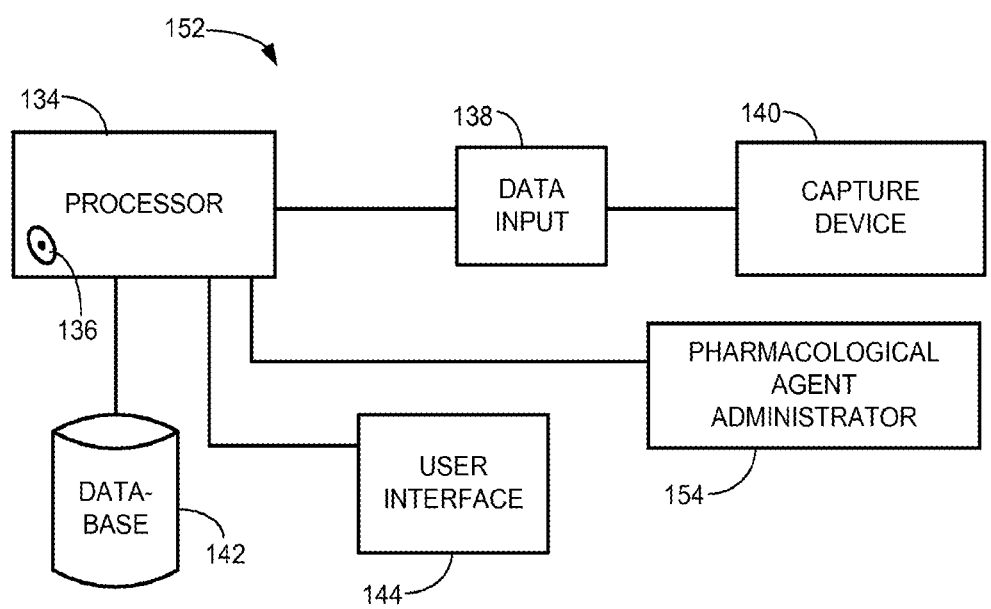

FIG. 17 schematically illustrates a further embodiment of a system 152 for evaluating an electrophysiological signal. In this embodiment, a data input 138, a user interface 144, and a database 142 are coupled to the processor 134. An electrophysiological signal capture device 140 is coupled to the data input 138. The system 152 also has a pharmacological agent administrator 154 which is coupled to the processor 134. The pharmacological agent administrator 154 may be configured to administer a pharmacological agent to a patient when enabled by the processor 134. The system 152 of FIG. 17, and its equivalents, may be useful in automating the analysis of the effects of pharmacological agents on patients with identified pathological events. A baseline pathological event can be identified from a baseline model-derived reconstruction of a baseline electrophysiological signal. Then, the processor 134 can instruct the pharmacological agent administrator 154 to administer a pharmacological agent. Then, a post-administration pathological event can be identified from a post-administration model-derived reconstruction of a post-administration electrophysiological signal. An effect of the pharmacological agent on a pathological event may be determined based on a comparison of the baseline pathological event and the post-administration pathological event.

Figure 18:
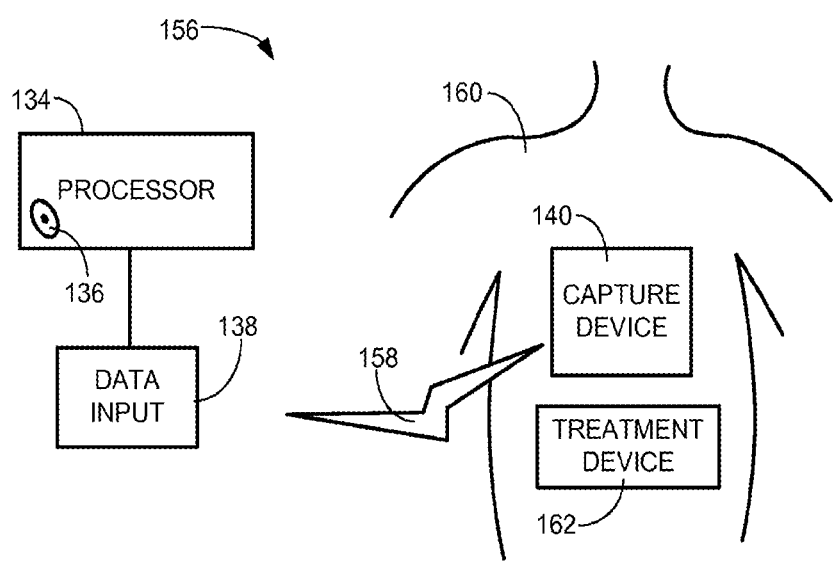

FIG. 18 schematically illustrates another embodiment of a system 156 for evaluating an electrophysiological signal. Similar to other embodiments, the system has a processor 134 which is coupled to a data input 138. An electrophysiological signal capture device 140 is coupled 158 to the data input 138. The coupling 158 may be wired or wireless. The electrophysiological signal capture device 140 is configured so that at least a portion of the electrophysiological signal capture device 140 is implantable in a subject's body 160. The processor 134 and the data input 138 are external to the subject's body 160 in this embodiment, however, in other embodiments, the processor 134 and/or the data input 138 could be partially or entirely implanted in the subject's body 160. The illustrated location of the implanted elements is merely for schematic illustration purposes and should not be considered limiting. The implanted elements may be located in any viable location of the body. The system 156 of FIG. 18 may optionally have a treatment device 162 coupled to the processor 134. In this case, the processor 134 may be configured to activate the treatment device 162 to attempt to correct or forestall an unfavorable clinical pathological event identified for the patient. Suitable examples of treatment devices 162 include, but are not limited to, a pharmacological agent administrator, a defibrillator, and an implantable brain device. The treatment device 162 may also be partially or completely implanted inside of the subject 160.

Noise Removal on a Z-Lead Using an FOS or a MFOS Model

The Discrete Fourier Transforms (DFT) is very good at producing a frequency distribution of power spectra for time series data. Unfortunately, when this technique is applied to biological time series data, which is inherently noisy, can be problematic since Fourier methods rely on equally spaced, complete data, and low noise for good characterization and cannot detect sub-harmonic frequencies. This is significant since these sub-harmonic frequencies exist in arrhythmia and are present proarrhythmic substrates when in sinus rhythm. To enhance the FFT, embodiments with the herein proposed use of the fast orthogonal search (FOS) and modified FOS (MFOS) methods are better suited to encode and characterize electrophysiological signal data, such as electrocardiogram (ECG) data.

Figure 19A:
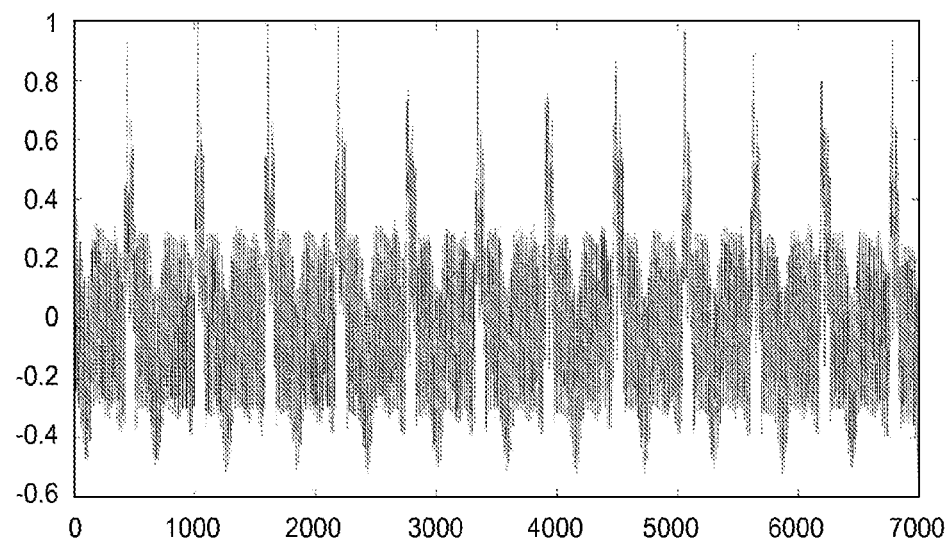
FIGS. 19A and 19B show ECG signal data before and after noise removal on the Z lead using a FOS model.
Figure 19B:
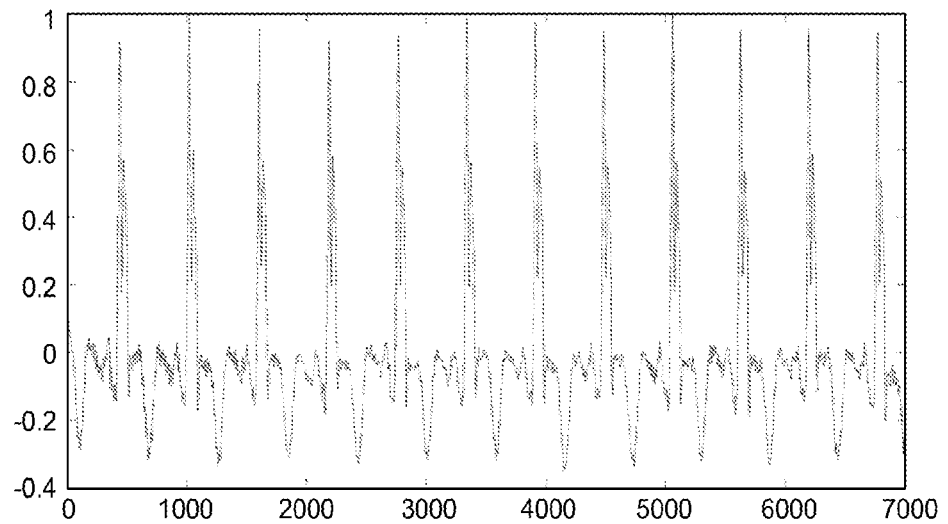

Key benefits of FOS and MFOS over other Spectral Analysis programs are: 1) FOS and MFOS achieve a higher spectral resolution, and 2) FOS and MFOS make use of a stopping criteria, therefore preventing the correlation of 'White Random Noise' that may be resident in the signal or signals being analyzed for key frequency content. FOS builds a functional expansion of an input signal by employing implicit orthogonal functions, "Orthogonal terms are fitted to minimize the mean square error of the orthogonal functional expansion." Subsequently, FOS and MFOS then potentially have a respective frequency resolution of up to twenty times of what the Discrete Fast Fourier Transform (DFT), or Wavelet method can yield, so notably, the FOS and MFOS algorithms may play a critical role in sensitive detection systems that have to be able to select-out critical frequency signatures of interest and remove reoccurring noise. The FOS and MFOS algorithms create frequency models of past detected highly correlated frequencies, and then compare the latest model against the most previous model. The comparison process continues until there is no energy left in the signal, and the subsequent mean square error values for both the orthogonal functions against a predetermined bottom threshold are met. The threshold is selected to prevent attempts to correlate unwanted biological signals or 'random noise' that may be present in the ECG signal. In addition, biological noise from breathing muscles and external noise and those from communication devices, switching power supplies, and terrestrial power lines can be detected and excluded or attenuated by customizing FOS and MFOS. This can be done by identifying noise terms in the FOS and MFOS models that are common to all ECG leads. These noise terms can be excluded from the FOS rebuilt signal as shown in FIG. 19B which has had noise removal on the Z lead using a FOS model (as compared to the signal shown in FIG. 19A before noise removal).

Applying the FOS or MFOS algorithm to ECG data will provide an enhancement to the current clinic methods of using Wavelets and FFT, since the FOS and MFOS methods can be customized to extract data from a surface ECG with a very high signal to noise ratio. A customized version of FOS or MFOS has the potential to identify high frequency components and sub components in atrial flutter, atrial fibrillation, ventricular tachycardia, and heart blocks with a vastly improved spectral response and noise rejection. This enhanced FOS or MFOS model will provide a discrete-time and frequency model of the heart that may be used to confirm physical features of heart conduction.

The disclosed methods and systems have provided valuable results when performed in real-world experiments.

Figure 20A:
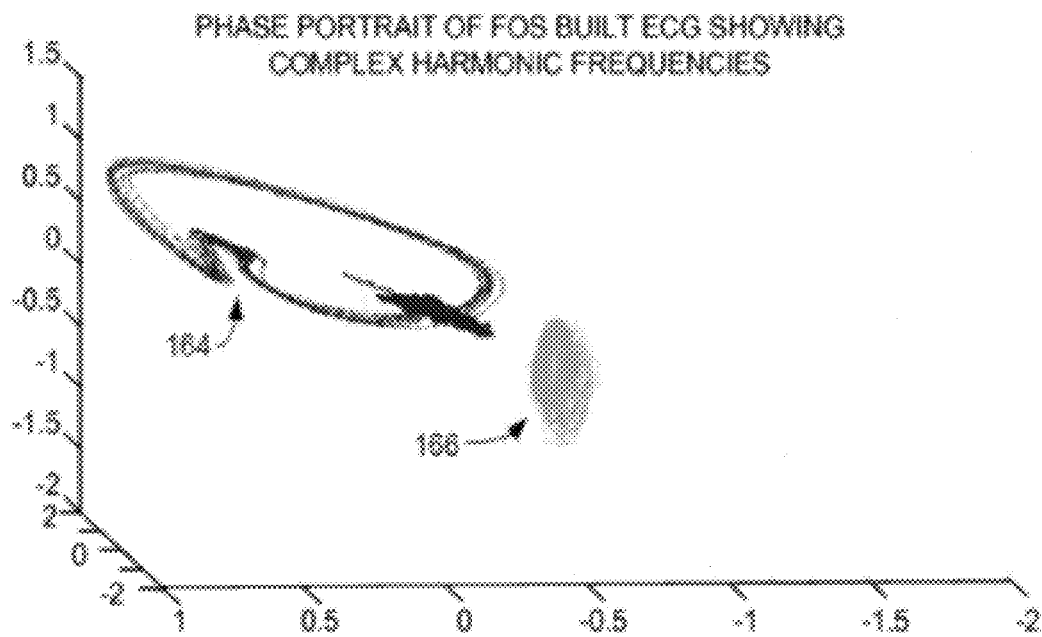
FIGS. 20A-20D illustrate Phase Portrait experimental data for a 14 year old girl with a large ventricular septal defect.
Figure 20B:
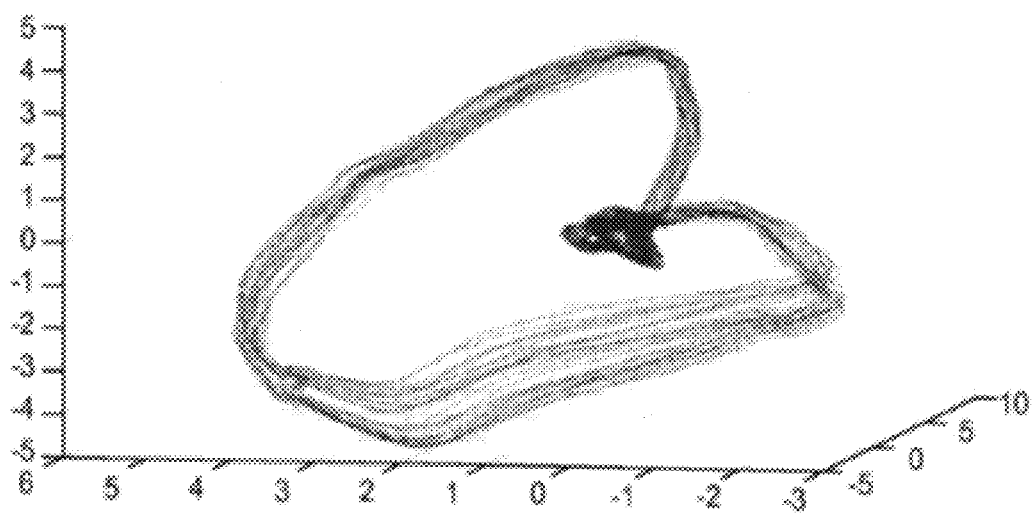
Figure 20C:
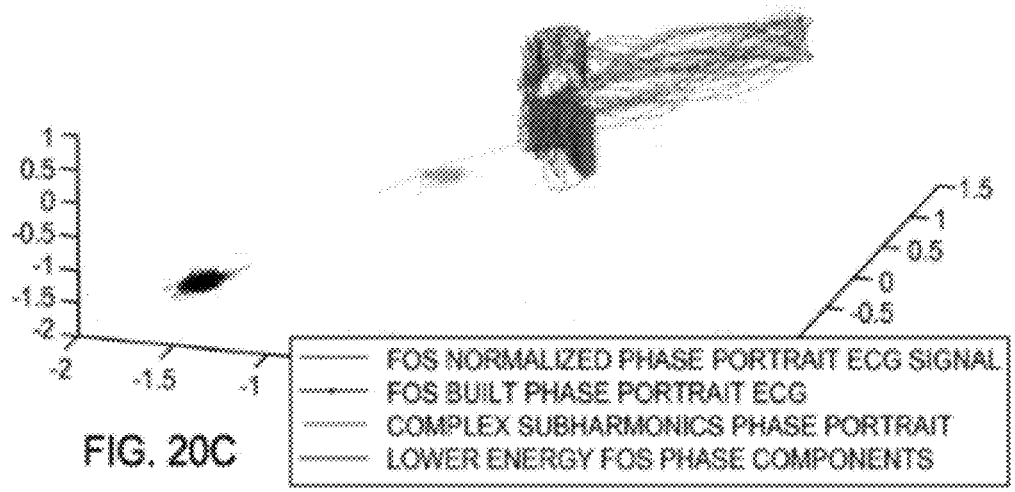
Figure 20D:
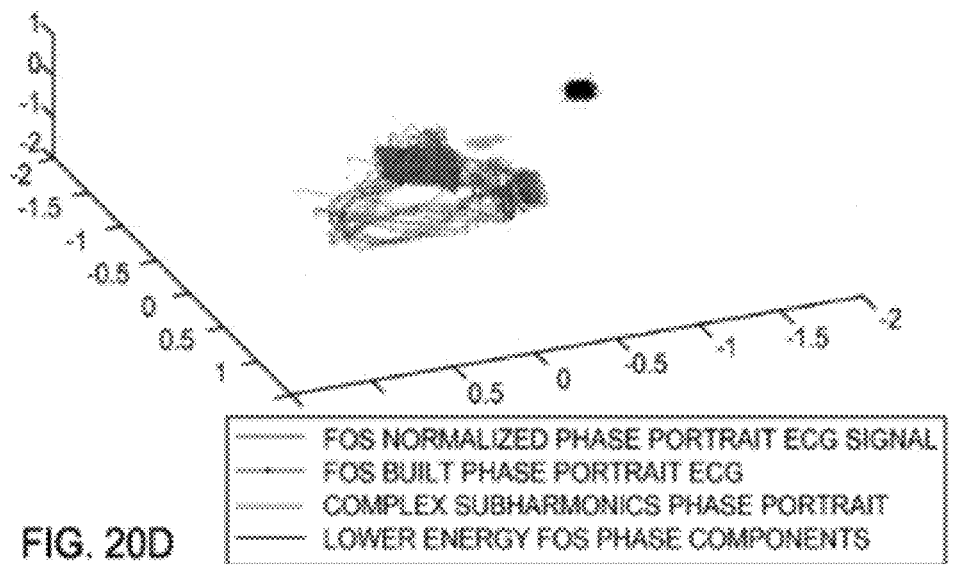

Experimental Results:

Confirming Physical Features of Heart Conduction in Proarrhythmic Substrates when in Sinus Rhythm:

FIG. 20A illustrates a Phase Portrait, produced using the methods disclosed herein to remove noise, for a 14 year old girl with a large ventricular septal defect. The septal defect can clearly be seen on the phase portrait of FIG. 20A. The electrophysiological signal (in this case, ECG data) was taken just after surgery to correct the septal defect. The tissue had not healed and the hole is still clearly showing as a notch 164 in the phase space portrait. The complex subharmnic region 166 has a tornadic shape which is a strong indicator of reentry (electrical whirlpool) around the corrected septal defect. Shortly after surgery she went into multiple episodes of ventricular tachycardia and was stabilized with medication. FIG. 20B shows the septal defect beginning to heal rapidly and show normal conduction. By comparison, FIGS. 20C and 20D show phase plots without the noise correction enabled with the methods disclosed herein, further complicated by the fact that the data was captured in part from a bad lead. It is next to impossible to make meaningful determinations from the phase space plots which were produced without the disclosed methods to remove the noise.

Conclusions:

Myocardial infarction (MI) and its subsequent ventricular remodeling creates altered electrophysiological (EP) substrates that can be highly arrhythmogenic. Current noninvasive methods for assessing abnormal EP substrates rely on ECG measurements from the body surface potentials. Traditional methods cannot provide detailed EP information about the cardiac substrate. Intrinsic Phase Space ECG imaging (PSECGi), as disclosed herein, is a noninvasive computational method for reconstructing EP information on the heart surface from simple 3-lead orthogonal body surface measurements. Experimental and clinical data from infarcted hearts have helped to define measures for identifying abnormal EP substrates and for stratifying their arrhythmogenic potential. Identification of arrhythmogenic substrates before an arrhythmia occurs could reduce the risk of sudden death by indicating the need for a drug, device, or ablation therapy. An ICD study was used to evaluate the ability of PSECGi to noninvasively locate and characterize abnormal cardiac EP substrates associated with myocardial infarction. This technology can be extended for its application to patients with ischemic, congenital disease and other forms of cardiomyopathy in adults and examine its ability to detect and characterize abnormal hearts.

An automated method of reducing noise associated with electrophysiological signals is valuable in the determination of a pathological process. In some embodiments, Fast orthogonal search (FOS) and MFOS can be used to model ECG data, and the FOS-found terms have been used experimentally to reconstruct the ECG with great fidelity and compression (~30:1) while rejecting white noise without using filtering. This technique detected and rebuilt the original ECG's corrupted by 40% additive Gaussian noise. FOS and MFOS can also be used as a selective nonlinear filter to remove terrestrial electromagnetic noise (e.g. 60 Hz line noise) and baseline drift that is common with ECG recordings associated with movement of the patient during recordings.

Transform an ECG into a vectrocardiogram (VCG): The standard ECG uses 12 leads positioned as it was found optimal from the medical point of view during a hundred years of practice. The VCG uses 3 channels connected in a orthogonal lead arrangement. FOS and MFOS models can be used for converting 12-lead ECG into (3 orthogonal XYZ channels) 3-lead vectorcardiography, or vice versa. Traditionally this transform requires the use of algorithms like Karhunen-Loeve, Dower, and Levkov convert VCG to ECG. FOS based transformation provides efficient compression, white noise removal, and removal of baseline drift with lossless conversion of ECG into a vectrocardiogram (VCG), or vice versa.

Specific groups of mathematical FOS and MFOS terms can be used to generate other subspaces of the 3D ECG signals. These subspaces are linked to specific properties of a non-linear system. In this case of ECG signals specific 3D subspaces have been linked to the determination of pathology. These subspace elements when quantified beat-to-beat in magnitude using a phase space clustering algorithm can be used to classify and predict heart arrhythmias and other heart abnormalities.

Use FOS or MFOS to compress the ECG: This compression ratio is calculated based on the number of points in the data versus the size of the frequency and amplitude array. It has been shown experimentally possible to compress the ECG with great fidelity at a ratio of 30 to 1. The nature of this compression is superior to that used in prior art methods, such as the method disclosed in Hazem Al. Abbas. Time series analysis for ECG data Compression. Acoustics, Speech, and Signal Processing, 1999. ICASSP '99. Proceedings., 1999 IEEE International Conference on Publication Date: 15-19 Mar. 1999, since the ECG does not require segmentation.

The brain is linked to the autonomic nervous system which amongst many systems in the body controls heart rate and cardiac output. Heart rate variability analysis traditionally requires observing variability of the R-R interval. Fast orthogonal search (FOS) and MFOS can be used to model the entire signal 3D ECG data and this can be used to generate other subspaces of the 3D ECG signal which can replace traditional variability analysis. These subspaces are linked to specific properties of a parallel cascade of non-linear systems and as such can be used to model the states of the brain and the heart. More specifically the disclosed methods and associated apparatus for evaluating electrophysiological signals may sensitively and specifically predict current and future pathological events such as heart disease, diabetic autonomic neuropathy, cardiac arrhythmias, Parkinson's disease, epilepsy, brain injury/disorders and altered states of cognition such as bipolar disorder and attention deficit disorder (ADD).

FOS and MFOS generated subspaces can be used to extract the fetal ECG from an ECG recorded on the mother's abdomen. The algorithm consists of two steps: first, ECG of fetus is extracted from the original signal using a 3D FOS or MFOS transform, then the Maternal ECG represents the remaining subspace energy.

Dynamical modeling of the 3D ECG will produce a moving 4D dynamical model of the 3D ECG using FOS and MFOS to transform the signal into the Phase Space domain. This represents the ability to model the systems stability dynamically at different heart rates from the data collected from a resting ECG. ECG signal is transformed into variable time domain with higher or lower heart rates. Corresponding stability scores (Lyapunov exponent) may be recalculated to determine the maximum and minimum patient heart rate based on bifurcation maps.

Figure 21A:
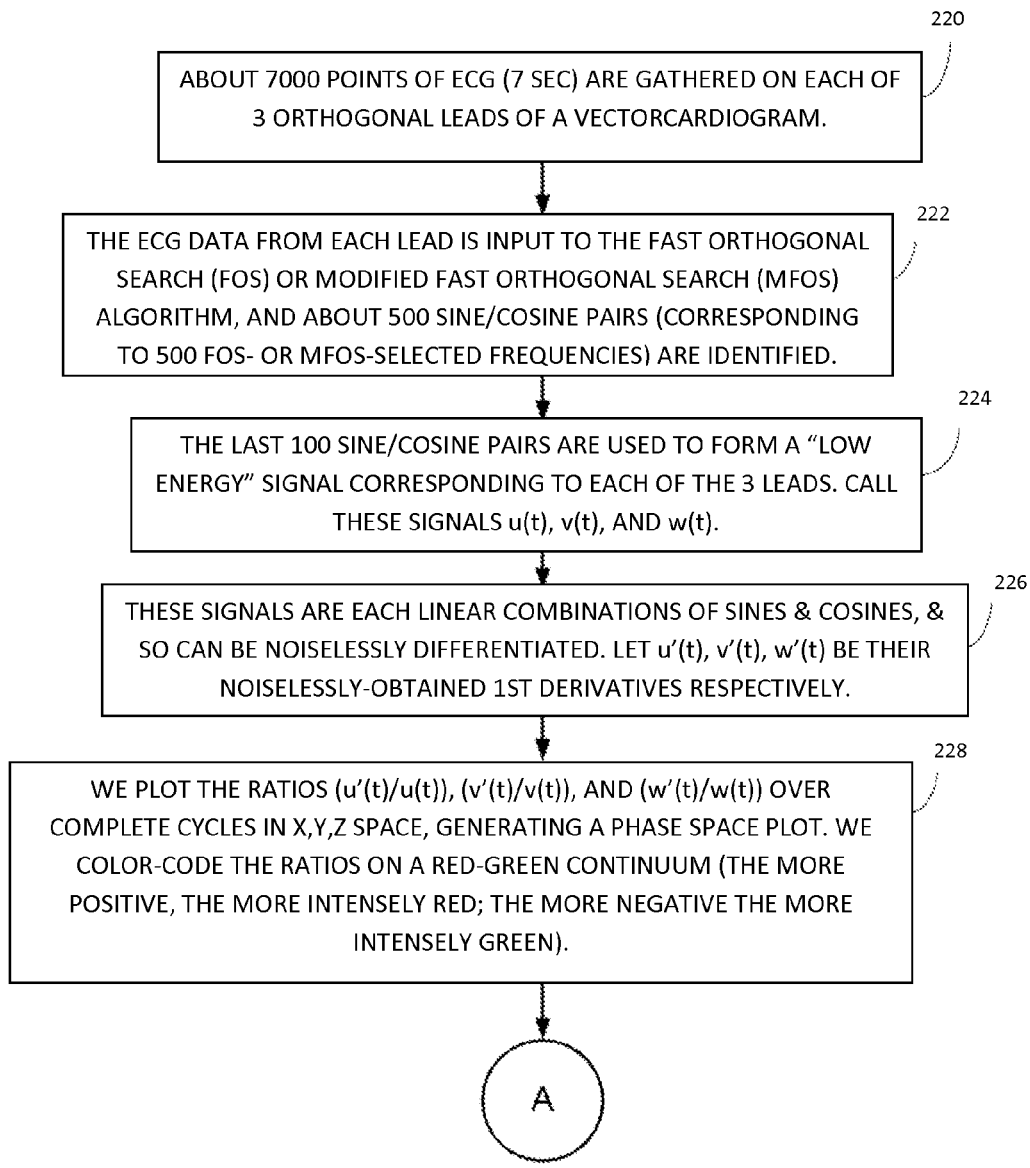
FIGS. 21A-21B are a flow diagram illustrating steps involved in one embodiment of a non-invasive method for locating an abnormality in the heart in accordance with an embodiment of the claimed invention.

FIGS. 21A,B form a flow diagram illustrating steps involved in one embodiment of a non-invasive method for locating an abnormality in the heart in accordance with an embodiment of the claimed invention. In step 220, ECG measurements are taken. In this embodiment, about 7000 points of ECG data (7 sec) is gathered on each of 3 orthogonal leads of a vectorcardiogram. Other embodiments may use a fewer or greater number of sample points. Other embodiments may use additional leads beyond the 3 orthogonal leads. Also, while the leads are said to be orthogonal, this is only an approximation and orthogonality is not essential. Moreover, for the same fixed finite record length for each of the lead signals, the Gram-Schmidt or other orthogonalization process can be used to create mutually orthogonal signals from the lead signals.

In step 222, the ECG data from each lead is input to the fast orthogonal search (FOS) or to the modified fast orthogonal search (MFOS) algorithm, and about 500 sine/cosine pairs (corresponding to 500 FOS-selected or MFOS-selected frequencies) are identified. A fewer or greater number of sine/cosine pairs may be identified and/or used in other embodiments.

In step 224, the last 100 sine/cosine pairs are used to form a "low energy" signal corresponding to each of the 3 leads. These low energy signals can be called u(t), v(t), and w(t).

In step 226, these signals are each linear combinations of sines and cosines, and so can be noiselessly differentiated. Let u'(t), v'(t), w'(t) be their noiselessly-obtained 1st derivatives respectively.

In step 228, the ratios (u'(t)/u(t)), (v'(t)/v(t)), and (w'(t)/w(t)) are plotted over complete cycles in X,Y,Z space, generating a phase space plot. We color-code the ratios on a red-green continuum (the more positive, the more intensely-red; the more negative the more intensely green).

There are a couple of points about the low-energy component (made from the last, say, 100 terms found by FOS or by MFOS) that are interesting and useful. First, we can find noiselessly the derivative of this component, since it is a linear combination of sine and cosine terms, and this derivative can be useful as a diagnostic tool, or to predict clinical outcome, and to view in X, Y, Z space. In addition, there are some useful ratios to consider. Thus suppose that u(t), v(t), and w(t) are respectively the X, Y, and Z coordinates of the low-energy component and let u'(t), v'(t), w'(t) be their 1st derivatives. Then the ratios:

(u'(t)/u(t)), (v'W/v(t)), and (w'(t)/w(t))

are like Lyapunov exponents and can indicate instability when positive. Consider the regions when the ratios are positive, especially when all are. In such regions, the magnitudes of u, v, w will increase. For example, if u is then positive, it will grow to a larger positive value because its derivative u' is positive, and if instead u is negative it will move downward to a negative value of larger magnitude because u' is negative. So these regions will indicate instability, and timing when they occur, and for how long, can be good ways of distinguishing between various cardiac conditions or, e.g., distinguishing shocked from non-shocked ICD patients. Of course, the same discussion applies when exponentially-decaying sines and cosines are used, since these can also be noiselessly differentiated.

In step 230, segments that look most deeply and alarmingly red will be where the positive ratios dominate (or maybe all tend to be positive) and indicate instability, while segments that are neutral in hue tend to be regions where the positive ratios tend to offset negative ones, or all the ratios are close to zero, while the most green segments are when the negative ratios dominate (or maybe all tend to be negative) and indicate stability. Timing in the cycle when the signal is most deeply red, & for how long, will help to distinguish between different cardiac conditions and, may, e.g., distinguish between different arrhythmias such as atrial fibrillation and ventricular fibrillation.

In step 232, the phase space plot information is then superimposed on a 3D representation of the heart to show where the red (alarming) areas are located in the interior or exterior of the heart and show where the damaged areas are in the heart. Timing in the cardiac (heart beat) cycle when the red alarming regions occur enables locating the corresponding regions of the heart where the abnormality is located. A lookup table can be prepared to facilitate going from the timing information to the location in the heart.

In step 234, integration involving corresponding portions of different FOS- OR MFOS-based phase space orbits can be used to estimate left and right atrial and ventricular wall thickness. Linear combinations of sines and cosines and some other nonlinear functions, found for example by FOS or MFOS, can be noiselessly integrated (Marcia Kleinz and Thomas J. Osler, "A Child's Garden of Fractional Derivatives", The College Mathematics Journal, Vol. 31, No. 2 (March, 2000), pp. 82-88). It is well-known (Korenberg, 1989 Biological Cybernetics, cited above) that FOS-found sinusoidal series are typically non-Fourier because the FOS series are not limited to use of a fundamental frequency and integer multiples (harmonics) of the fundamental.

Such ECG-based methods of estimating chamber sizes are well-known in the literature. For example, Van Beeumen et al. ("Changes in P-wave area and P-wave duration after circumferential pulmonary vein isolation", Europace (2010) 12, 798-804) found that reduction in electrical atrial tissue results in marked decrease in P-wave area. Also, Lerman and Basson ("Topics in Structural Heart Disease", Demos Medical Publishing, Dec. 11, 2009) report the finding that the area under the QRS complex, i.e. the time-voltage integral, can improve estimates of left ventricular mass. De Jong and Bouhiouf (P Wave Morphology—ECGpedia, http://en.ecgpedia.org/index.php?title=P_Wave_Morphology&oldid=11179, accessed Mar. 18, 2014) write that "If the p-wave is enlarged, the atria are enlarged", and give examples of how altered P-wave morphology can distinguish between normal versus right atrial enlargement versus left atrial enlargement. In the section "Chamber Hypertrophy and Enlargment" (http://en.ecgpedia.org/wiki/Hypertrophy, accessed Mar. 21, 2014) de Jong discusses ECG-based ways of distinguishing between left versus right ventricular hypertrophy and between left versus right atrial enlargement.

Discussion of Other, Non-Limiting Embodiments:

The above discussion, and in particular the same discussion in steps 226 and 228 above, applies when FOS or MFOS, or any other method is used to find linear combinations of exponentially-decaying sines and cosines or any other functions that can also be noiselessly differentiated. The discussion also applies to other FOS- or MFOS-derived or otherwise obtained signals that can be noiselessly differentiated, e.g. u'(t), v'(t), w'(t) can themselves be noiselessly differentiated, to yield their second derivatives, respectively u"(t), v"(t), w"(t). These derivatives, or those of arbitrary order, can be useful as a diagnostic tool, or to predict clinical outcome, and to view in X, Y, Z space. Alternatively, we can instead plot the new ratios (u"(t)/u'(t)), (v"(t)/v'(t)), and (w"(t)/w'(t)) over complete cycles in X,Y,Z space, generating another phase space plot. Here a positive value of a new ratio indicates when the derivative of the corresponding signal u(t), v(t), or w(t) is increasing in magnitude, and can mean an increase in frequency and thus a potential for arrhythmia onset. The same discussion applies to derivatives of arbitrary order and, also, to corresponding ratios.

The u(t), v(t), and w(t) may each correspond to other than the low-energy signal, but rather to other FOS- or MFOS-derived signals (or signals obtained by other methods), e.g. the FOS or MFOS model outputs corresponding to the signals from the original 3 leads, or to signals constructed from FOS- or MFOS-found frequency components within specified frequency ranges.

Figure 21B:
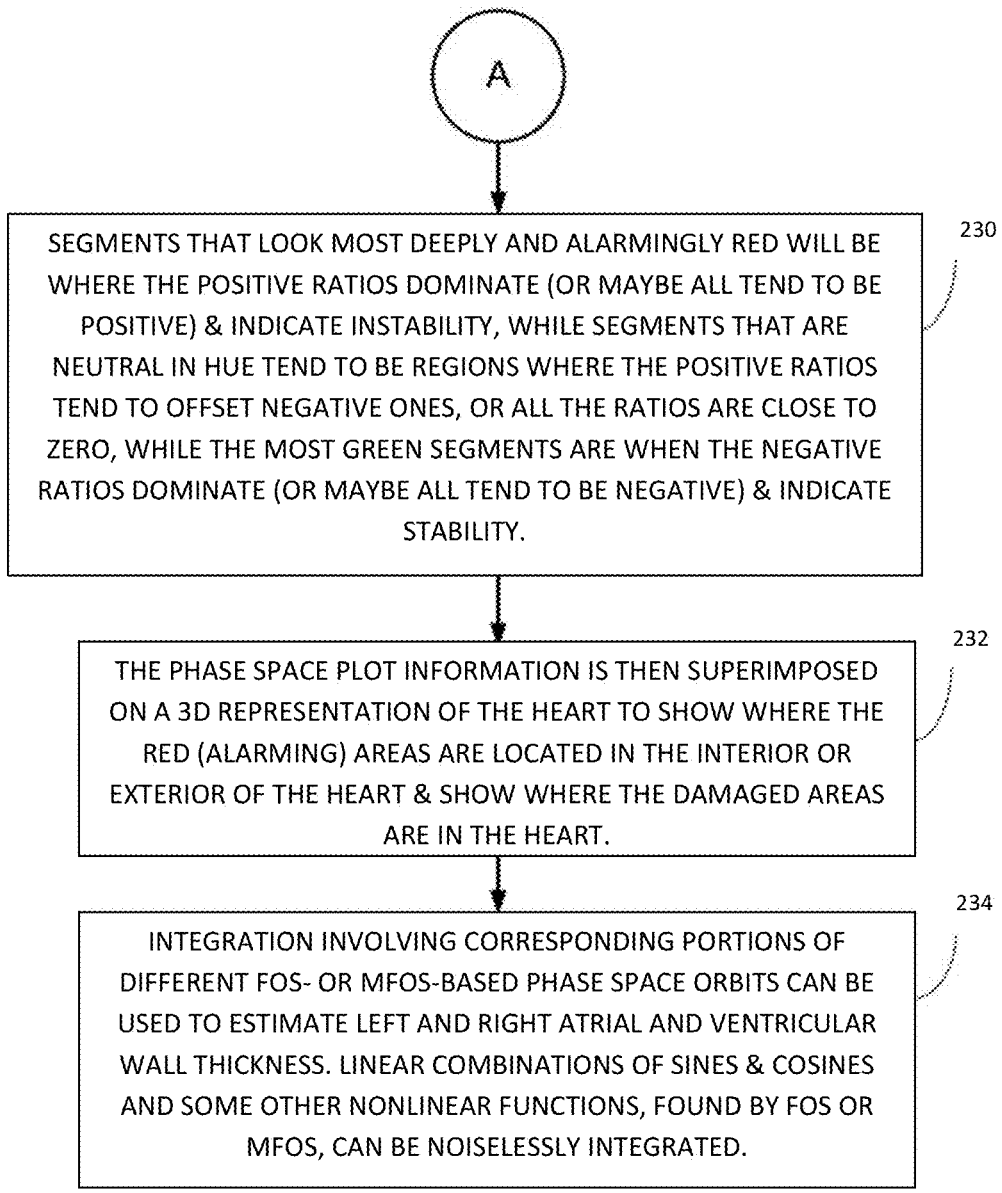

Timing in the cardiac (heart beat) cycle when the red alarming regions occur enables locating the corresponding regions of the heart where the abnormality is located. The ECG data comprises at least one heart beat cycle and the abnormality in the heart can be detected within a particular time interval within the heart beat cycle (e.g., see step 230 in FIG. 21B), and such time interval is used in detecting the location of the abnormality within the heart. Indeed, the heart beat cycle corresponds to an electrical pathway through the heart, and this pathway is used with the time interval where the abnormality has been detected in determining the location of the abnormality in the heart.

The way weighted k-nearest neighbors can be used with a radio map to determine one's position in an indoor environment can also be used to rapidly locate the damaged area in the heart. The radio map is prepared by measuring the signal strength of possibly hundreds of access points (APs, i.e. transmitters) at many locations in the building. FOS can be used to reduce the number of APs that need be used to a small number, say 4, and get even better positioning than using all the APs. This is described in the paper by M. M. Atia, M. J. Korenberg, A. Noureldin, "Fast features reduction of radio maps for real-time fingerprint-based wireless positioning systems", Electronics Letters, Vol. 47(20), pp. 1151-1153, 2011, which is hereby incorporated by reference in its entirety. To determine one's position in the building, measure the signal strength of these 4 APs, and find the closest k "matches" on the radio map to the measured power pattern, then weighted-average the k locations (positions in the building) corresponding to the k closest matches. The closer the match is to the measured signal strength, the more its position is weighted in computing the average over the k closest matches. The k closest matches are called the k-nearest neighbors. We can analogously position the damage within the heart of a new patient. The timing of where the damage shows up on the phase space diagram tells us approximately where it is in the heart (and the better the correspondence is known between the diagram and the path through the heart, the better our initial positioning). We then use the X, Y, Z ECGs and/or FOS model outputs corresponding to the "damaged" region on the phase space plot and find the closest k matches to stored X, Y, Z ECGs and/or FOS model outputs where the damaged areas in the heart are known. We use the known positioning of the heart damage for these k closest matches to position the damage in the heart of the new patient. The more we build up a database where the damage positions in the heart have been accurately calculated already or have been otherwise determined, the more accurate will be the positioning in the new patient's heart.

Aside from use of color, other schemes can be employed to indicate the problematic or alarming areas in a diagram or figure (e.g. image of heart). For example if we plot the stability ratios:

(u'(t)/u(t)), (v'(t)/v(t)), and (w'(t)/w(t))

over complete cycles, we can code them on a dotted line to solid line, and/or light nearly-white to black line, and/or thin to wide line continuum (e.g. the more positive the ratios, the more heavy dark wide solid line; the more negative the ratios the more light thin dotted line). Then, for example, segments that look most deeply and alarmingly wide, dark, solid line will be where the positive ratios dominate (or maybe all tend to be positive) and indicate instability, while segments that are medium in thickness and/or in grayness tend to be regions where the positive ratios tend to offset negative ones, or all the ratios are close to zero, while the thinnest, lightest, and/or dotted segments are when the negative ratios dominate (or maybe all tend to be negative) and indicate stability.

Other methods than use of the ratios can detect abnormal areas in phase space diagrams. For example, FOS signals corresponding to the 3 leads can be plotted in phase space along with the actual signals corresponding to these leads, and significant divergence of a FOS signal from the corresponding lead signal can indicate an abnormal area.

Other measures that can be plotted in phase space include estimates of the Lyapunov exponent, computed by using corresponding points of a plurality of cardiac (heart beat) cycles, such as at the P, R, and T peaks and at intervening points. Again, color coding can denote when these estimates are positive, indicating instability, and this new phase space information can be used to display the abnormal region in an image of the heart.

Images can be created that zoom in on one portion of the heart, e.g. the left or right atrium or ventricle. For example, suppose that a few points have been sampled around each successive R peak to calculate Lyapunov exponent (instantaneous and average values) to predict ventricular instability. In addition to making this prediction, the result of sampling these points can be treated as a time series to be analyzed by FOS. So if 5 values are sampled around each of, say, 300 successive R peaks, there will be a 1500-point time series to submit to FOS or to MFOS. Also note the timing when each sample is taken, so that there will be 1500 pairs of (sampling time, value), since the samples are not equally spaced. Then use a FOS or MFOS program that does not require equally-spaced time series values. The modification is simple: replace sample number n by the sampling time t[n] of the n-th sample, in the candidate sines and cosines or complex exponentials or other candidate functions. Once FOS or MFOS has been run, the result can be used in several ways. Suppose the first half of the time series is used to find the FOS or MFOS model. Then the resulting model can be used to predict the second half of the time series and see how close it is to the actual one. A significant divergence between the actual and the predicted time series can indicate an abnormal area. One can calculate Lyapunov exponent, both instantaneous and average values, to study the departure between the model-predicted and the actual time series values, and see if the exponent is positive. Graphically displaying in X,Y,Z phase space the model-predicted and actual time series may also show striking differences between those with versus without ventricular arrhythmias or instability, and one can look at the MSE of the fit. Also FOS can be applied to the entire time series and show how close the FOS model output is to the actual time series, to determine the extent of divergence and to calculate Lyapunov coefficients, etc. Also, one can see what differences in frequencies are found for those with ventricular arrhythmias or instability versus those without these problems. Similarly, one can do all these things to study atrial instability or arrhythmias. The idea is to submit to FOS or MFOS a time series composed of the points sampled only around the portion of the ECG record of interest, e.g. around successive R peaks, or around successive P waves. This makes the FOS or MFOS running times much shorter. Thus, start with an entire ECG record, then throw out all portions of the record except those that concern what is to be studied or imaged, e.g. atrial or ventricular behavior. FOS and MFOS are capable of dealing with the resulting unequally-spaced data.

In place of using orthogonal leads in step 220 above, other leads can be selected from standard 12 lead ECG. For example, FOS can be used to improve on Principal Component Analysis (PCA), and find a concise set of ECG leads to use out of the 12 leads, rather than a few most important PCA-found eigenvectors (each eigenvector would involve all of the 12 leads). Thus, FOS can be used as an alternative to PCA, but FOS has the huge advantage that the features selected have physical meaning, unlike the eigenvectors found by PCA. For example, one can use FOS to select from 12 leads ECG the 1, 2, 3, or 4 leads that are the most important, and the FOS-selected leads may carry more information than those used in a vectorcardiogram. See paper (M. J. Korenberg and K. M. Adeney, "Iterative Fast Orthogonal Search for Modeling by a Sum of Exponentials or Sinusoids", Annals of Biomedical Engineering, Vol. 26, pp. 315-327, 1998) especially on pages 324-325, the section on FITTING MULTIPLE SETS OF OBSERVATIONS, which paper is hereby incorporated by reference in its entirety. A key idea here is that when data are available from multiple experiments, one may select the SAME basis functions (out of the candidates) to fit all the experimental data, but the coefficients used in the linear combination of basis functions may vary from one experiment to another. Suppose there are 12 leads, and for each lead 7000 points of data (the number of sampled points is immaterial). Maybe some of the leads carry most of the useful information and others are virtually redundant. In this example there is a 7000 row by 12 column data matrix. One wants to see if just a few leads can be used to predict the values of the remaining leads. Each column is a 7000×1 vector that will be one of 12 candidate functions. In the 1st experiment, the 1st column is the desired (target) output, in the 2nd experiment the 2nd column is the desired output, etc. One chooses one concise set out of the candidate functions to fit the data from ALL experiments (the coefficients will change from one experiment to the next, but this is allowed— use Eqs 17,18 in the above-referenced 1998 Korenberg and Adeney paper). One can be more general by allowing crossproducts in the candidates but the explanation will be kept simple here. It is very important that ONE concise subset of model terms is selected from the candidate functions to fit the data from ALL the experiments (again see Eqs 17, 18). Of course, one can also try this repeatedly using less than 12 candidates at a time, by searching through different candidate subsets each time. A nice result is that if one finds a few key leads (rather than super-leads that PCA would find), they have physical meaning, e.g. the selected leads are ones actually applied to the patient and may serve as indicators of what are the key places to sample the electrical activity of the heart. Perhaps these selected leads distinguish well between survivors and non-survivors of MIs in particular places in the heart, or between those with and without Atrial Fibrillation, or between responders and non-responders to particular treatments—so some leads may be better than other leads depending upon the patient population. Of course other model-building techniques besides FOS and MFOS can be used with this strategy of treating the lead signals as if they form multiple sets of observation, while the lead signals also form the candidate functions. For example, the methods known as least angle regression (LARS), LASSO (R. Tibshirani, "Regression shrinkage and selection via the lasso", Journal of the Royal Statistical Society, Series B (Methodological), Vol. 58(1), 1996, pp. 267-288), and iterative fast orthogonal search (IFOS, see above-referenced 1994 article by Adeney and Korenberg) may be used.

Another way to use this FOS alternative to PCA is to prepare a data matrix where the columns are particular indicators of cardiac function (e.g. T-wave alternans, heart rate variability, HRT, QRS width, ejection fraction, etc and crossproducts thereof including powers), and the rows are for different patients. Maybe rows 1-20 are for MI survivors and 21-40 for MI non-survivors. Again the columns are the candidate functions, and in the first experiment, the first column is the desired output, in the second experiment the second column is the desired output, etc. The model terms are the few, say 3, columns selected to fit the data from ALL experiments. These selected 3 columns may distinguish well between the survivors and non-survivors (e.g. survivors may group in one region of the reduced dimensional space spanned by the selected 3 columns while non-survivors group in a different region). If so, then there could be a simple test to predict survivors versus non-survivors. Note that this method does not require access to ECG recordings. Thus FOS can be used to examine many measures (e.g. T-wave alternans, heart rate variability, HRT, QRS width, ejection fraction) and see which measures may be redundant for a particular population, say survivors and non-survivors of MI or Congestive Heart Failure.

There is another way that FOS can be used to find terms that are predictive of clinical outcome, again without needing access to ECG recordings. The "Refine" study by Exner et al (J. Am. Coll. Cardiol. 2007; 50; 2275-2284) tested the capability of certain individual parameters, e.g. heart rate variability, HRT, QRS width, ejection fraction, TWA, history of diabetes, to predict outcomes such as cardiac death in early post-MI periods. As a non-limiting example, if the output (clinical outcome) of a surviving patient is defined as −1, and that of a dying patient is defined as 1, then FOS can be used to find specific combinations (e.g. certain crossproducts) of the individual parameters that may have much greater power predicting outcome. In a recently-published study of heat-related emergency department visits (A. G. Perry, M. J. Korenberg, G. G. Hall, and K. M. Moore, "Modeling and Syndromic Surveillance for Estimating Weather-Induced Heat-Related Illness", Journal of Environmental and Public Health, Volume 2011, Article ID 750236, 10 pages, doi: 10.1155/2011/750236) FOS was able to find models with unusual crossproduct terms that were good predictors of visits. In the present application of predicting clinical outcome, e.g. sudden cardiac death or all-cause mortality, the FOS or MFOS model terms would be selected from the individual parameters considered in the Refine study, other measures of cardiac function, and cross-products thereof. Depending on the number of factors in the cross-product terms, there may be 1000s of candidate terms, but FOS and MFOS can within minutes build a concise model with unobvious terms that are good indicators of the clinical outcome. A huge advantage of this approach is that it enables using together many different previously proposed indicators of cardiac function and making new predictors by FOS- or MFOS-selected combinations and cross-products of existing indicators. To use FOS or MFOS to find new predictive combinations of individual parameters, one needs access to the individual parameter values for each patient, together with the corresponding clinical outcome.

FOS and MFOS can be used to improve on PCA, and find a concise set of genes rather than a few most important eigenvectors (supergenes that would involve all of the genes). See above-referenced 1998 paper by M. J. Korenberg and K. M. Adeney, ("Iterative Fast Orthogonal Search for Modeling by a Sum of Exponentials or Sinusoids", Annals of Biomedical Engineering, Vol. 26, pp. 315-327, 1998) at pages 324-325 section on FITTING MULTIPLE SETS OF OBSERVATIONS. The key idea here is that when data are available from multiple experiments, one may select the SAME basis functions (out of the candidates) to fit all the experimental data, but the coefficients used may vary from one experiment to another. Suppose there are 40 patients, and for each patient there are 6000 points representing the expression levels of the same 6000 genes. Maybe 20 patients responded well to treatment and 20 did not. Hence there is a 40 row by 6000 column data matrix. One wants to see if just a few genes can be used to predict the expression levels of the remaining genes. Each column is a 40×1 vector that will be one of 6000 candidate functions. In the first experiment, the first column is the desired output, in the second experiment the second column is the desired output, etc. Then choose one concise set of basis functions to fit the data from ALL experiments (the coefficients of the selected basis functions will change from one experiment to the next, but this is permitted—use Eqs 17, 18 in the above 1998 paper). One can be more general by allowing crossproducts in the candidates but the explanation is kept simple here. It is very important that ONE concise set of basis functions is selected to fit the data from ALL the experiments (again see Eqs 17, 18). Of course, one can also try this repeatedly using less than 6,000 candidates at a time, by searching through different candidate subsets each time. A nice result is that if one finds a few key genes (rather than supergenes), they have physical meaning, e.g. the selected genes can serve as targets for drugs, or the proteins these genes code for can have therapeutic value. Perhaps these selected genes distinguish well between responders and non-responders to treatment (e.g. responders may group in one region of the reduced dimensional space spanned by the selected genes while non-responders group in a different region). If so, then this would provide a simple gene test to predict response to a particular proposed treatment. Alternatively, maybe the rows are for, say, 20 women who have ovarian cancer, and 20 who do not. Then the selected genes may distinguish well between these 2 groups, and so there would be an effective gene expression test to detect ovarian cancer. Of course the same approach can be applied to distinguish between women known to have the BRCA1 (or BRCA2) mutation and those known not to have the mutation. The same approach can also be applied with single nucleotide polymorphisms (SNPs) data, DNA sequences, and any other biologic profile data.

A "circular" spiral can be used to explore and compare 2D, 3D, or higher dimensional images, and has an advantage that the resulting metrics describing the image can be relatively insensitive to rotations of the 2D, 3D, or higher dimensional image about the center of the spiral. For the 3D case, an example of such a spiral, whose center is the origin, is given by the parametric equations, $$X(t)=R(t)\cos(w1(t))\sin(w2(t)),$$

$$Y(t)=R(t)\cos(w1(t))\cos(w2(t)),$$

$$Z(t)=R(t)\sin(w1(t)),$$

where $X(t)$, $Y(t)$, $Z(t)$ are the coordinates of a point on the spiral, and $R(t)$, $w1(t)$, $w2(t)$ are each non-negative monotonically increasing functions of t. For a "tighter" spiral, $R(t)$ increases more slowly,
relative to $w1(t)$, $w2(t)$, than for a "looser" spiral. For example, for corresponding values of t, one may compute the Euclidean distance between the spiral and the image, and discover which spiral shape best-fits the image. This approach can be used to distinguish between images for patients at higher versus lower risk of adverse clinical outcome.

Embodiments discussed have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention.

Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A method of detecting an abnormality in a patient from an electrophysiological signal, comprising:
   a) obtaining an electrophysiological signal corresponding to the patient;
   b) finding, using a processor of a computing device, a model corresponding to the electrophysiological signal wherein at least one term in the model is differentiable;
   c) obtaining the derivative of the at least one term; and
   d) using the derivative over at least one cycle of the electrophysiological signal in order to detect the abnormality.

2. The method of claim 1, wherein the derivative has an order, and wherein the order is a real number.

3. The method of claim 2, wherein the order of the derivative is a positive number.

4. The method of claim 3, wherein the order of the derivative is a positive integer.

5. The method of claim 1, wherein the at least one model term has a derivative of order a and also of order a−1, and wherein a ratio of the derivative of order a to the derivative of order a−1 exists over a plurality of points over at least one cycle of the electrophysiological signal.

6. The method of claim 5, wherein the order a is a positive integer, and wherein the ratio is used over at least one cycle of the electrophysiological signal in order to detect the abnormality.

7. The method of claim 6, wherein the ratio is displayed over at least one cycle of the electrophysiological signal to form a plot, and wherein one or more highlighted indicators are used in the plot to indicate those portions where the ratio is positive.

8. The method of claim 7, wherein the electrophysiological signal is a portion of an electrocardiogram, and wherein the plot is placed over a portion of a 3-D outline of the heart, and wherein one or more highlighted indicators are used to indicate the areas in the interior or exterior of the heart where damaged areas are in the heart.

9. A method for building a model approximating an electrophysiological signal, wherein the method includes choosing a measure of approximating the signal, wherein the method involves using a processor of a computing device in a search through candidate terms to select terms to add to the model at successive stages, and wherein at least two distinct candidate terms are selected, where one of the selected terms causes, out of the candidate terms searched, the greatest reduction in the measure of approximating the signal, and another of the selected terms causes, out of the candidate terms searched, at least one of: a relative maximum of the reduction of the measure of approximating the signal; and a reduction of the measure of approximating the signal above a specified threshold level.

10. The method of claim 9, further comprising:
    a) receiving the electrophysiological signal at a computing device;
    b) selecting, at the computing device, a plurality of terms for the model approximating the electrophysiological signal;
    c) separating a noise component from the plurality of terms selected for the model; and
    d) forming a reconstructed electrophysiological signal whereby the noise component is removed by using a subset of the plurality of terms selected for the model.

11. The method of claim 9, wherein at least one of the at least two candidate terms that are selected is a complex exponential.

12. The method of claim 9, further comprising:
    applying a modified fast orthogonal search (MFOS) transform to the electrophysiological signal to generate a plurality of terms corresponding to the electrophysiological signal; and
    forming a reconstructed electrophysiological signal whereby a noise component is separated from the electrophysiological signal using a subset of the plurality of terms, corresponding to the electrophysiological signal, which have at least a desired compression ratio.

13. The method of claim 1, wherein the electrophysiological signal comprises a portion of an electrocardiogram including portions of at least two lead signals, wherein an orthogonalization process is used to create at least two mutually orthogonal signals from the portions of the at least two lead signals, and wherein the at least two mutually orthogonal signals are used in place of the portions of the at least two lead signals.

14. The method of claim 1, wherein the electrophysiological signal comprises portions of at least two signals measured at corresponding instants of time, wherein the derivative is used in a mathematical expression that is applied to each of the at least two signals at corresponding instants in time to obtain positive or negative indications of the abnormality, wherein the expression is used to form a plot corresponding to different instants of time, and wherein one or more highlighted indicators are used to indicate segments of the plot when the expression detects the abnormality, said highlighted indicators comprising at least one of:
  color coded indicators, including use of a first and a second color such that the first color dominates at instants when negative indications of the abnormality dominate, the second color dominates at instants when positive indications of the abnormality dominate, and the highlighted indicator is closer to neutral in hue at instants when positive indications of the abnormality are offset by negative indications of the abnormality; and
  shaded indicators, one or more type of broken line, and one or more type of line thickness.

15. The method of claim 8, wherein the highlighted indicators comprise at least one of color coded indicators, shaded indicators, one or more type of broken line, and one or more type of line thickness.

16. The method of claim 9, wherein the measure of approximating the signal involves at least one of the error, the square error, the mean square error, the weighted mean square error, the maximum square error, and the perpendicular distance to a hyperplane.

17. The method of claim 2, wherein a function of the derivative is defined, wherein the function of the derivative assumes at least one value over a plurality of points over at least one cycle of the electrophysiological signal, and wherein at least one representation of the at least one value is displayed over the plurality of points.

18. The method of claim 3, wherein a function of the derivative is defined, wherein the function of the derivative assumes at least one value over a plurality of points over at least one cycle of the electrophysiological signal, and wherein at least one representation of the at least one value is displayed over the plurality of points.

19. A method of using a model-building procedure to select a concise subset of electrocardiogram (ECG) leads to use out of a larger set of ECG leads, comprising:
  a. for each lead in the larger set, using the corresponding lead signal to define a candidate signal;
  b. for each lead in the larger set, using the corresponding lead signal to define a desired target output signal from an experiment; and
  c. selecting the same subset of lead signals, out of the candidate signals, to approximate all the target signals from all the experiments by linear combinations of the selected lead signals, while allowing the coefficients of the selected lead signals to vary in approximating the target signals from one experiment to another.

20. The method of claim 19, wherein selecting the same subset of lead signals uses at least one of fast orthogonal search (FOS), modified fast orthogonal search (MFOS), least angle regression (LARS), LASSO, and iterative fast orthogonal search (IFOS).

* * * * *